United States Patent
Allen et al.

(10) Patent No.: US 11,401,424 B2
(45) Date of Patent: Aug. 2, 2022

(54) AGE-RESISTANT ASPHALT COMPOSITIONS AND METHODS

(71) Applicant: Blacklidge Emulsions Inc., Gulfport, MS (US)

(72) Inventors: Robert Grover Allen, Biloxi, MS (US); Henry Cuevas, Long Beach, MS (US); Roy Brittany Blacklidge, Gulfport, MS (US)

(73) Assignee: Blacklidge Emulsions, Inc., Gulfport, MS (US)

( * ) Notice: Subject to any disclaimer, the term of this patent is extended or adjusted under 35 U.S.C. 154(b) by 788 days.

(21) Appl. No.: 15/844,838

(22) Filed: Dec. 18, 2017

(65) Prior Publication Data

US 2018/0171146 A1 Jun. 21, 2018

Related U.S. Application Data

(60) Provisional application No. 62/436,306, filed on Dec. 19, 2016.

(51) Int. Cl.
 *C08L 95/00* (2006.01)
 *C10C 3/02* (2006.01)
 (Continued)

(52) U.S. Cl.
 CPC ............. *C08L 95/00* (2013.01); *C10C 3/026* (2013.01); *G01N 33/42* (2013.01);
 (Continued)

(58) Field of Classification Search
 CPC .............................. C08L 95/00; C08L 95/005
 See application file for complete search history.

(56) References Cited

U.S. PATENT DOCUMENTS 2,802,798 A * 8/1957 Smith ................. C08L 2666/02
   524/62
5,769,567 A 6/1998 Durand et al.
(Continued)

FOREIGN PATENT DOCUMENTS

| CA | 1321276 C | 8/1993 |
| EP | 2487207 A2 | 8/2012 |
| WO | 2016170083 A1 | 10/2016 |

OTHER PUBLICATIONS

Bitumen in colloid science: a chemical, structural, and rheological approach. Fuel vol. 77, Issue 13, Oct. 1998, pp. 1443-1450. https://doi.org/10.1016/S0016-2361(98)00054-4. Loeber et al. (Year: 1998).*

(Continued)

*Primary Examiner* — Alexandra M Moore
(74) *Attorney, Agent, or Firm* — Patterson Intellectual Property Law, P.C.; William E. Sekyi

(57) ABSTRACT

Aging resistant asphalt compositions and related methods of preparing and applying the same are provided. The aging resistant asphalt compositions can include a base asphalt with specified properties combined with an aging resistance additive, to produce modified asphalt compositions having a colloidal index within the range of about 3.7 to about 8.0, a saturates content of less than about 10% by weight, and measurable age-resistant properties. The aging resistant asphalt compositions are useable in a variety of asphalt paving and non-paving applications. The aging resistant asphalt compositions provide improved resistance to both moderate and low failure temperatures of conventional paving asphalts throughout its service life by reducing age-related failures.

26 Claims, 6 Drawing Sheets

(51) Int. Cl.
    G01N 33/42    (2006.01)
    G01N 3/60    (2006.01)
(52) U.S. Cl.
    CPC ....... C08L 2555/10 (2013.01); C08L 2555/64
           (2013.01); C08L 2555/72 (2013.01); G01N
              3/60 (2013.01); Y02A 30/30 (2018.01)

(56) References Cited

U.S. PATENT DOCUMENTS

| | | | | |
|---|---|---|---|---|
| 2003/0191212 | A1* | 10/2003 | Yamazaki | C08L 95/00 524/59 |
| 2009/0133604 | A1 | 5/2009 | Fischer et al. | |
| 2010/0275817 | A1 | 11/2010 | Williams et al. | |
| 2012/0063843 | A1 | 3/2012 | Blacklidge | |
| 2015/0008156 | A1* | 1/2015 | Martin | C08L 95/00 208/23 |
| 2016/0362338 | A1* | 12/2016 | Reinke | C08L 91/00 |
| 2017/0137717 | A1* | 5/2017 | Palmer | C08L 95/00 |

OTHER PUBLICATIONS

PCT search report and opinion of PCT application No. PCT/US2017/067138, dated May 15, 2018, 16 pages.
Amy L. Epps, Charles J. Glover, and Roberto Barcena, A Performance-Graded Binder Specification for Surface Treatments, Research: Aug. 1999-Aug. 2001, Report Date: Oct. 2001, 70 pages, FHWA/TX-02/1710-1, Texas Department of Transportation Research and Technology Implementation Office, Austin, Texas.
NAPA, Performance Graded Asphalt Binder Specification (from AASHTO MP 1), Dec. 9, 2017, 1 page, Virtual Superpave Laboratory, The National Asphalt Pavement Association, Landam, Maryland, Lanham, MD.
R. Michael Anderson, Gayle N. King, Douglas I. Hanson, and Phillip B. Blankenship, Evaluation of the Relationship between Asphalt Binder Properties and Non-Load Related Cracking, 2011, 35 pages, Abstract, Airfield Asphalt Pavement Technology Program, Auburn, Alabama.
Y. Ruan, R. R. Davison and C. J. Glover, An Investigation of Asphalt Durability: Relationships between Ductility and Rheological Properties for Unmodified Asphalts, Petroleum Science and Technology, 2003, 25 pages, Abstract, Marcel Dekker, Inc., New York, New York.
Robert Grover Allen, Microstructural Characterization of the Chemomechanical Behavior of Asphalt in Terms of Aging and Fatigue Performance Properties, A Dissertation, May 2013, 162 pages, Office of Graduate Studies of Texas A&M University, College Station, Texas.
The Asphalt Institute, The Use of REOB/VTAE in Asphalt, State-of-the-Knowledge, Apr. 12-13, 2016, 92 pages IS-235, The Asphalt Institute's Technical Advisory and Health, Safety & Environment Committees, Lexington, Kentucky.
R. Grover Allen, Upping the Ante: What Binder Modification Can do to Impact Performance, NAPA Paving for Performance "Designed to Perform", Oct. 13, 2017, 31 pages, Blacklidge Emulsions, Douglasville, Georgia.
Scott Shuler, Anthony Lord, Amy Epps-Martin, Denise Hoyt, Manual for Emulsion-Based Chip Seals or Pavement Preservation, National Cooperative Highway Research Program Report 680, 2011, 110 pages, National Academy of Sciences, Washington, DC.
Geoffrey Rowe, Prepared discussion for the AAPT paper by Anderson et al.: Evaluation of the relationship between asphalt binder properties and non-load related cracking, Journal of the Association of Asphalt Paving Technologists 80, 649-662, 2011, 11 pages, AAPT, Lino Lakes, Minnesota.
Zane L. Webb, Seal Coat and Surface Treatment Manual, May 1, 2010, 162 pages, Maintenance Division of the Texas Department of Transportation, Austin, Texas.
Prithvi S. Kandhal, Leo D. Sandvig and Monroe E. Wenger, Shear Susceptibility of Asphalts in Relation to Pavement Performance, Journal of the Association of Asphalt Paving Technologists, Asphalt Paving Technology vol. 42, 1973, 27 pages, Abstract, AAPT, Lino Lakes, Minnesota.
Prithvi S. Kandhal, Low-Temperature Ductility in Relation to Pavement Performance, Low-Temperature Properties of Bituminous Materials and Compacted Bituminous Paving Mixtures, American Society for Testing and Materials, 1977, 12 pages, Abstract, ASTM International, West Conshohocken, Pennsylvania.
Moon-Sun Lin, Jay M. Chaffin, Meng Liu, C.J. Glover, R.R. Davison and J.A. Bullin, The Effect of Asphalt Composition on the Formation of Asphaltenes and their Contribution to Asphalt Viscosity, 1996, 27 pages, Abstract, Department of Chemical Engineering, Texas A&M University, College Station, Texas.
Malcolm L. Williams, Robert F. Landel, and John D. Ferry, The Temperature Dependence of Relaxation Mechanisms in Amorphous Polymers and Other Glass-forming Liquids, Jul. 20, 1955, 7 pages, The Journal of the American Chemical Society, Washington DC.
Harold L. Von Quintus, Jag Mallela, and Jane Jiang, Expected Service Life and Performance Characteristics of HMA Pavements in LTPP, Final Report, Feb. 2005, 64 pages, Asphalt Pavement Alliance, Grange Park, Florida.
Prithvi S. Kandhal and William C. Koehler, Significant Studies on Asphalts Durability: Pennsylvania Experience, Transportation Research Record 999, 1981, 10 pages, Abstract, Transportation Research Board, Washington DC.
Australian Office Action for corresponding Patent Application No. 2017378888, dated Apr. 6, 2020, 6 pages.
Reinke et al., "Impact of re-refined engine oil bottoms on binder properties and mix performance on two pavements in Minnesota", E & E Congress 2016, 6th Eurasphalt & Eurobitume Congress, Jun. 1-3, 2016.
Shamborovskyy, "Development of a Fatigue-Based Asphalt Binder Purchase Specification for Airfield Asphalt", Graduate School—New Brunswick Rutgers, The State University of New Jersey, May 2016.
Office Action for corresponding Indian application No. 201917027015, dated Nov. 6, 2020, 6 pages.
European Office Action for corresponding EP 17 88 2948, dated Aug. 13, 2020, 7 pages.
Standard Method of Test for Effect of Heat and Air on a Moving Film of Asphalt Binder (Rolling Thin-Film Oven Test), AASHTO T 240-13 (2017), American Association of State Highway and Transportation Officials, 12 pages.
M.N. Siddiqui, M.F. Ali; "Studies on the aging behavior of the Arabian asphalts," Fuel 78 (1999), p. 1005-1015.

* cited by examiner

Asphalt Performance Grade (PG) Standards – Asphalt Institute.

| Max. Design Temp. | PG 46 | | | PG 52 | | | | | | | PG 58 | | | | | PG 64 | | | | | | PG 70 | | | | | | PG 76 | | | | | PG 82 | | | | |
|---|---|---|---|---|---|---|---|---|---|---|---|---|---|---|---|---|---|---|---|---|---|---|---|---|---|---|---|---|---|---|---|---|---|---|---|---|---|
| Min. Design Temp. | -34 | -40 | -46 | -10 | -16 | -22 | -28 | -34 | -40 | -46 | -16 | -22 | -28 | -34 | -40 | -10 | -16 | -22 | -28 | -34 | -40 | -10 | -16 | -22 | -28 | -34 | -40 | -10 | -16 | -22 | -28 | -34 | -10 | -16 | -22 | -28 | -34 |
| Original | | | | | | | | | | | | | | | | | | | | | | | | | | | | | | | | | | | | | |
| Flash Point = 230 °C | | | | | | | | | | | | | | | | | | | | | | | | | | | | | | | | | | | | | |
| Rotational Viscosity = 3 Pa-s @ 135°C | | | | | | | | | | | | | | | | | | | | | | | | | | | | | | | | | | | | | |
| DSR G*/sin δ (Dynamic Shear Rheometer) = 1.00 kPa | 46 | | | 52 | | | | | | | 58 | | | | | 64 | | | | | | 70 | | | | | | 76 | | | | | 82 | | | | |
| (Rolling Thin Film Oven) RTFO, Mass Change ≤ 1.00% | | | | | | | | | | | | | | | | | | | | | | | | | | | | | | | | | | | | | |
| DSR G*/sin δ (Dynamic Shear Rheometer) = 2.20 kPa | 46 | | | 52 | | | | | | | 58 | | | | | 64 | | | | | | 70 | | | | | | 76 | | | | | 82 | | | | |
| (Pressure Aging Vessel) PAV | | | | | | | | | | | | | | | | | | | | | | | | | | | | | | | | | | | | | |
| 20 hours, 2.10 MPa | 90 | | | 90 | | | | | | | 100 | | | | | 100 | | | | | | 100(110) | | | | | | 100(110) | | | | | 100(110) | | | | |
| DSR G*·sin δ (Dynamic Shear Rheometer) = 5000 kPa | | | | | | | | | | | | | | | | | | | | | | Intermediate Temp. = [(Max. + Min.)/2] + 4 | | | | | | | | | | | | | | | |
| | 10 | 7 | 4 | 25 | 22 | 19 | 16 | 13 | 10 | 7 | 25 | 22 | 19 | 16 | 13 | 31 | 28 | 25 | 22 | 19 | 16 | 34 | 31 | 28 | 25 | 22 | 19 | 37 | 34 | 31 | 28 | 25 | 40 | 37 | 34 | 31 | 28 |
| BBR S (creep stiffness) & m-value (Bending Beam Rheometer) S = 300 kPa; m = 0.300 | -24 | -30 | -36 | 0 | -6 | -12 | -18 | -24 | -30 | -36 | -6 | -12 | -18 | -24 | -30 | 0 | -6 | -12 | -18 | -24 | -30 | 0 | -6 | -12 | -18 | -24 | -30 | 0 | -6 | -12 | -18 | -24 | 0 | -6 | -12 | -18 | -24 |
| If BBR m-value = 0.300 and creep stiffness is between 300 and 600, the Direct Tension Failure strain requirement can be used in lieu of the creep stiffness requirement. | | | | | | | | | | | | | | | | | | | | | | | | | | | | | | | | | | | | | |
| DTT (Direct Tension Tester) $\varepsilon_f$ = 1.00% | -24 | -30 | -36 | 0 | -6 | -12 | -18 | -24 | -30 | -36 | -6 | -12 | -18 | -24 | -30 | 0 | -6 | -12 | -18 | -24 | -30 | 0 | -6 | -12 | -18 | -24 | -30 | 0 | -6 | -12 | -18 | -24 | 0 | -6 | -12 | -18 | -24 |

*FIG. 5 (Prior Art)*

AGE-RESISTANT ASPHALT COMPOSITIONS AND METHODS

CROSS-REFERENCE TO RELATED APPLICATIONS

This application claims the benefit of U.S. Provisional Application No. 62/436,306, filed on Dec. 19, 2016.

FIELD OF THE INVENTION

The present invention is generally directed toward improved asphalt compositions and related methods, and more specifically to asphalt compositions having improved age-resistant qualities and methods for making and using the same.

BACKGROUND OF THE INVENTION

Asphalt, also known commonly as asphalt cement, asphalt binder, binder, pitch, and/or bitumen, is a versatile material that is used in numerous applications, e.g., roofing shingles, pipe coatings, paints, water-proofing, and joint sealants, although, its primary use is in the construction of asphalt concrete ("AC") pavements. Asphalt is one of two primary components used in the construction of AC pavement layers. The other component is aggregate typically comprised of gravel and/or crushed stone. Asphalt is the flexible glue that binds the aggregates together to support heavy traffic loads. It is also the weak link in the AC mixture. Although aggregates comprise over 90% by weight of an AC mixture, it is asphalt—proportioned at approximately 4-8% of the AC mixture—which causes mix-related failure of AC pavements in the majority of cases.

Properly screened aggregates used in AC provide high volume stability, adequate bearing strength, and are themselves resistant to aging. Basically, an old aggregate is just as reliable as a new aggregate. Conversely, asphalts are complex mixtures of many different molecules, which can make predicting the chemical and physical properties of freshly produced asphalts difficult and predicting the change in properties of asphalts during service life even more difficult.

Initially upon mixing and placing the AC pavement into service, asphalt degrades and hardens significantly due to volatilization and other influences. This degradation continues via oxidation and other types of aging, including polymerization, thixotropy, syneresis, and separation relative to a variety of exposure factors including air, temperature, UV radiation, and water. Therefore, asphalt—the innately complex weak link in AC pavements—quickly loses ductility and relaxation properties, causing it to become weaker, more brittle, and more unpredictable over a relatively short period. The rate at which age hardening and breakdown of a particular asphalt occurs is well-known in the art to be highly variable and difficult to predict due to the extremely complex chemical nature of asphalt. Different crude sources, different crude refining processes, and even different batches from the same crude source refined using the same processes are all factors in manufacturing that are understood to affect unpredictability of asphalt ageing. Inclusion of asphalt additives designed to modify the physical and chemical properties of asphalt often add further unpredictability.

Differences between asphalts create many unknowns regarding expectations for aging resistance of the final AC product. What is known is that the majority of asphalts specified by agencies and used to build roadways show signs of aging and deterioration within approximately 12 years, and in many cases, in significantly fewer years. Chemists, chemical engineers, and civil engineers involved in asphalt research, development, and engineering have attempted for decades to draw correlations between asphalt chemistry and observed rheological properties and performance of AC pavements. One such approach to study asphalt chemistry is to divide asphalt into four unique fractions, SARA—Saturates, Naphthene Aromatics, Polar Aromatics (Resins), and Asphaltenes, according to ASTM D 4124-09. Despite extensive use of this method, no effective correlations have been developed to relate the various single chemical fractions (saturates, aromatics, resins, and asphaltenes) to their measured rheological properties. (Netzel, D. A., Miknis, F. P., Thomas, K. P., Wallace, Jr., J. C., and Butcher, C. H. Molecular Motions and Rheological Properties of Asphalts: An NMR Study. *Asphalt Science and Technology*, Chapter 2 pp. 11-58, Usmani, A., ed. (Marcei Dekker: New York, N.Y. 1997).

It is estimated that there are over 2.5 million miles of paved roads in the U.S. alone. Over 90% of them are paved with an asphalt composition, such as AC. Because of the wide variety of asphalts as well as the variation in their properties of different asphalts, industry has developed several classification systems to categorize asphalts based on various properties so that users can more easily select asphalts suitable for their needs.

The penetration grading classification system was developed in the early 1900 s to characterize the consistency of semi-solid asphalts. The key classifying measurement of this system is the penetration test, carried out at 25° C., which determines the depth (in 0.1 mm units) a standard needle penetrates an asphalt sample under a 100 g load. Penetration grading's basic assumption is that the less viscous the asphalt, the deeper the needle will penetrate. This penetration depth is empirically (albeit only roughly) correlated with asphalt binder performance. Therefore, asphalt binders with high penetration numbers (called "soft") are used for cold climates while asphalt binders with low penetration numbers (called "hard") are used for warm climates.

Subsequently, industry adopted a viscosity grading classification system which used a viscosity test as its key classifying measurement instead of the penetration test. The viscosity test typically measured the resistance to flow of asphalt at 60 C (approximately the maximum AC pavement temperature during summer in the U.S.) using a vacuum capillary viscometer. Viscosity grading can be done on original (as-supplied) asphalt binder samples (called AC grading) or aged residue samples (called AR grading). The AR viscosity test is based on the viscosity of aged residue from the rolling thin film oven ("RTFO") test. With AC grading, the asphalt binder is characterized by the properties it possesses before it undergoes the hot mix asphalt ("HMA") manufacturing process. The AR grading system is an attempt to simulate asphalt binder properties after it undergoes a typical HMA manufacturing process and thus, it should be more representative of how asphalt binder behaves in HMA pavements.

Because penetration grading and viscosity grading were somewhat limited in their ability to fully characterize asphalt binder for use in HMA pavement, researchers subsequently developed new binder tests and specifications to more accurately and fully characterize asphalt binders for use in HMA pavements known as Superpave Performance Grading ("PG"). PG tests and specifications are specifically designed to address HMA pavement performance parameters such as rutting, fatigue cracking and thermal cracking.

Superpave performance grading is based on the idea that an HMA asphalt binder's properties should be related to the conditions under which it is used. For asphalt binders, this involves expected climatic conditions as well as aging considerations. Therefore, the PG system uses a common battery of tests as the older penetration and viscosity grading systems but specifies that a particular asphalt binder must pass these tests at specific temperatures that are dependent upon the specific climatic conditions in the area of use. Thus, test criteria remain constant, however, the temperature at which the criteria must be met changes in consideration of the binder grade selected for the prevalent climatic conditions.

The PG system also calls for testing to be performed under specific conditions to simulate three critical binder ages: 1) original asphalt binder prior to mixing with aggregate; 2) aging representative of the asphalt binder after HMA production and application to form a paved surface; and 3) aging representative of long-term (approximately 3-7 years) aged binder. To be classified under a particular PG grade, asphalt must pass a range of binder tests including: rolling thin film oven (RTFO), pressure aging vessel (PAV), rotational viscometer (RV), dynamic shear rheometer (DSR), bending beam rheometer (BBR), and in some instances the direct tension tester (DTT). Tests are run on the original binder (no simulated aging), RTFO residue (simulated short-term aging) and PAV residue (simulated long-term aging of about 7 years) in order to fully characterize the asphalt binder during the earlier portion of its intended life. FIG. 5 lists specification parameters that the asphalt binder must meet for each corresponding test and temperature. Often, the same test is run on different simulated binder ages. For instance, the DSR is run on all three simulated binder ages, although the desired criteria at the different aging states may differ.

Under the PG system, the RTFO procedure provides simulated short term aged asphalt binder for physical property testing. Asphalt binder is exposed to elevated temperatures to simulate manufacturing and placement aging. The RTFO also provides a quantitative measure of the volatiles lost during the aging process. The basic RTFO procedure takes unaged asphalt binder samples in cylindrical glass bottles and places these bottles in a rotating carriage within an oven. The carriage rotates within the oven while the 325° F. (163° C.) temperature ages the samples for 85 minutes. Samples are then stored for use in physical properties tests or the PAV.

Under the PG system, the PAV procedure provides simulated long term aged asphalt binder for physical property testing. Asphalt binder is exposed to heat and pressure to simulate in-service aging. Although some originally believe that the PAV procedure simulates aging over a 7 to 10 year period, others now believe the PAV procedure is more representative of 3 to 7 years of in-service aging. For purposes of the instant application, it is understood that the basic PAV procedure represents 7 years of in-service aging. The basic PAV procedure takes RTFO aged asphalt binder samples, places them in stainless steel pans and then ages them for 20 hours in a heated vessel pressurized to 305 psi (2.10 MPa or 20.7 atmospheres). Samples are then stored for use in physical property tests.

Superpave performance grading is reported using two numbers—the first being the average seven-day maximum pavement temperature (° C.) and the second being the minimum pavement design temperature likely to be experienced (° C.). Thus, a PG 58-22, for example, is intended for use where the average seven-day maximum pavement temperature is 58° C. and the expected minimum pavement temperature is −22° C.

Despite these systems for classifying and selecting asphalts for use in paving applications, the durability and service lives of many of these roads are limited by pavement failures and distress that become more prevalent as the pavement ages. A failure mode that is significant in many of these pavements is surface-initiated distress. Asphalt aging is a root cause of surface-initiated distress, which includes various types of cracking and raveling.

Known methods for improving the durability and quality of asphalts do not adequately address these shortcomings in asphalt and AC. Some in the industry have suggested methods of upgrading the quality of asphalt by using a cracking-resistance additives. Some references have proposed that any alkylated aromatic can be used as an additive to any asphalt and suggest using especially poor quality asphalts having a T10 boiling point of at least 900° F. and use only 0.1 wt % to 5 wt % of the alkylated aromatic additive. Some advocates of using these alkylated aromatic crack-resistant additives suggest that when using up to 2% or up to 5% by weight in the asphalt composition, the high temperature performance grade ("PG") of the resulting asphalt composition in which the additive is blended will typically not decrease at all and will at most decrease by 1° C. or 2° C.

However, merely adding an aromatic such as an alkylated aromatic to poor quality asphalt would likely be insufficient to improve the asphalt's ability to resist cracking due to aging. First, virtually all asphalts contain at least 30% aromatics, including alkylated aromatics, and in many cases this number is beyond 50%, prior to the addition of any additive, and yet many of these asphalts are highly susceptible to aging and cracking defects. Second, additives blended with or added to asphalt in which the additive contains at least one aromatic have been used in asphalt applications for decades. These conventional approaches demonstrate a well-known practice in the industry to introduce an aromatic oil to particular asphalts, which dates back to at least the 1960's, and have had little or no success in providing the industry with a viable age-resistant asphalt composition.

Various publications actually discourage the use of aromatic oils in asphalt. Some note that conventional practice has been to add softer asphaltic compounds or aromatic oils or other additives to soften or plasticize the asphalt composition. In order to reach acceptable low temperature properties, excessive amounts of soft asphaltic materials or fluxes must be added. Because of the large quantities of aromatic oils normally required in these asphalt compositions and the consequent increased aromaticity from the oil, the mixtures typically include large quantities of polymers to achieve sufficient rutting resistance. However, the large quantities of polymer typically included in these compositions renders them undesirably costly and infeasible. In fact, there are many additives containing aromatic oils that can cause severe harm to aging, cracking, and rutting resistance of asphalt, making the asphalt altogether unsuitable for a paving composition. Thus it is well known that not all alkylated aromatics are suitable for use with asphalts used in AC or other paving applications.

There is a need to provide an asphalt composition with high resistance to age-hardening degradation processes that work to weaken asphalt and AC pavement. There is also a need to provide methods of developing the same.

SUMMARY OF THE INVENTION

In one aspect, modified asphalt compositions comprising a base asphalt and an aging resistance additive that effectively resist aging-related failures are provided. In some embodiments, the modified asphalt compositions have a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition that is less than about 5.5° C. The base asphalt may comprise between about 80% and about 99.9% by weight of the modified asphalt composition in some embodiments. The base asphalt may be selected from non-paving grade asphalts including hard pen asphalts, conventional paving grade asphalts, and mixtures thereof. In some embodiments, the aging resistance additive comprises about 0.1% to about 20% by weight of the modified asphalt composition. In some embodiments, the aging resistance additive is an oil blend with a SARA fraction composition of about 55% to about 80% by weight naphthene aromatics and about 10% to about 30% by weight polar aromatics.

In some preferred embodiments, the modified asphalt compositions have a penetration value of between about 40 dmm and about 220 dmm at 25° C. In other preferred embodiments, the modified asphalt compositions have a SARA fraction composition of about 40% to about 60% by weight naphthene aromatics, about 25% to about 45% by weight polar aromatics, about 3% to about 8% by weight saturates, and about 3% to about 15% by weight asphaltenes. In some preferred embodiments, the modified asphalt compositions have a paraffin wax level of less than about 0.5%. In particularly preferred embodiments, the modified asphalt compositions further meet or exceed minimum specification requirements for a conventional paving grade asphalt to be replaced by the asphalt composition. In further preferred embodiments, the minimum specification requirements comprise a paving asphalt grade selected from the group consisting of penetration graded asphalts of between about 40 dmm to about 220 dmm at 25° C. according to ASTM 5-13/AASHTO T49-15, AC-graded asphalts AC-2.5, AC-5, AC-10, AC-20, AC-30, and AC-40 according to ASTM D3381-12 (Table 2 or Table 4 equivalents), AR-graded asphalts AR-1000, AR-2000, AR-4000, AR-8000, and AR-16000 according to ASTM D3381-12, and premium PG grades PG 82-28, PG 82-22, PG 82-16, PG 76-28, PG 76-22, PG 76-16, PG 70-28, 70-22, 70-16, PG 67-28, PG 67-22, PG 67-16, PG 64-28, PG 64-22, PG 64-16, PG 58-34, PG 58-28, PG 58-22, PG 58-16, PG 52-40, PG 52-34, PG 52-28, PG 52-22, and PG 52-16 according to AASHTO M 320-16. In still further preferred embodiments, the modified asphalt compositions have a measured difference between a high-temperature PG grade failure temperature from an original sample of the modified asphalt composition and a high-temperature PG grade failure temperature from an RTFO-aged residue sample of the modified asphalt composition that is less than 1.5° C. In yet further preferred embodiments, the modified asphalt compositions have a measured ΔTc of an RTFO plus 60-hour PAV-aged residue sample of the modified asphalt composition is between about 2.5° C. and about −5.0° C. In still further preferred embodiments, the modified asphalt compositions have a measured ΔTc of an RTFO plus 40-hour PAV tested aged residue sample of the modified asphalt composition that is between about 2.5° C. and about −3.0° C. In yet further preferred embodiments, the modified asphalt compositions have a measured change in BBR failure temperature of an RTFO plus 20-hour PAV-aged residue sample of the modified asphalt composition and an RTFO plus 40-hour PAV-aged residue sample of the modified asphalt composition that is less than about 2.5° C. In yet further preferred embodiments, the modified asphalt compositions further comprise an aggregate. In particularly preferred embodiments, the aggregate is added to the modified asphalt composition after the modified asphalt composition is applied to a roadway surface structure to create a chip seal. In particularly preferred embodiments, the modified asphalt compositions further comprise a conventional asphalt additive selected from the group consisting of hardeners, plastomers, and elastomers including, but not limited to, ethylene vinyl acetate (EVA), vinyl acetate-ethylene (VAE), styrene-butadiene-styrene (SBS), styrene butadiene (SB), styrene-butadiene rubber (SBR), SBR Latex, polychloroprene, isoprene, polybutadiene, acrylic, acrylic copolymers, ground tire rubber (GTR), terpolymers, crumb rubber modifier (CRM), polyphosphoric acid (PPA), natural or synthetic waxes, GILSONITE (also known as uintaite), Trinidad Lake asphalt, and other modifiers that are well-known in the industry and commonly used for the purpose of adding elastomeric properties, strength, and/or "grade-bumping" for asphalt compositions, and any combination of the foregoing.

In another aspect, modified asphalt compositions prepared by a process comprising mixing a base asphalt and an aging resistance additive that effectively resist aging-related failures is provided. In some embodiments, the modified asphalt compositions have a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition that is less than about 5.5° C. In some preferred embodiments, the modified asphalt compositions have a SARA fraction composition of about 40% to about 60% by weight naphthene aromatics, about 25% to about 45% by weight polar aromatics, about 3% to about 8% by weight saturates, and about 3% to about 15% by weight asphaltenes. In some preferred embodiments, the modified asphalt compositions have a measured ΔTc of an RTFO plus 60-hour PAV-aged residue sample of the modified asphalt composition that is between about 2.5° C. and about −5.0° C.

In yet another aspect, methods of preparing a modified asphalt composition comprising mixing a base asphalt and an aging resistance additive that effectively resist aging-related failures are provided. In some embodiments, the prepared modified asphalt compositions have a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition is less than about 5.5° C. The base asphalt may comprise between about 80% and about 99.9% by weight of the modified asphalt compositions in some embodiments. The base asphalt may be selected from non-paving grade asphalts including hard pen asphalts, conventional paving grade asphalts, and mixtures thereof. In some embodiments, the aging resistance additive comprises about 0.1% to about 20% by weight of the modified asphalt composition. In some embodiments, the aging resistance additive is an oil blend with a SARA fraction composition of about 55% to about 80% by weight naphthene aromatics and about 10% to about 30% by weight polar aromatics. In some embodiments, the aging resistance additive has a colloidal index of greater than about 7.0 and less than about 100.

In some preferred embodiments, the prepared modified asphalt composition has a penetration value of between about 40 dmm and about 220 dmm at 25° C. In other preferred embodiments, the prepared modified asphalt composition has a SARA fraction composition of about 40% to about 60% by weight naphthene aromatics, about 25% to about 45% by weight polar aromatics, about 3% to about 8% by weight saturates, and about 3% to about 15% by weight asphaltenes. In some preferred embodiments, the prepared modified asphalt composition has a paraffin wax level of less than about 0.5%.

In particularly preferred embodiments, the prepared modified asphalt composition further meets or exceeds minimum specification requirements for a conventional paving grade asphalt to be replaced by the asphalt composition. In further preferred embodiments, the minimum specification requirements comprise a paving asphalt grade selected from the group consisting of penetration graded asphalts of between about 40 dmm to about 220 dmm at 25° C. according to ASTM 5-13/AASHTO T49-15, AC-graded asphalts AC-2.5, AC-5, AC-10, AC-20, AC-30, and AC-40 according to ASTM D3381-12 (Table 2 or Table 4 equivalents), AR-graded asphalts AR-1000, AR-2000, AR-4000, AR-8000, and AR-16000 according to ASTM D3381-12, and premium PG grades PG 82-28, PG 82-22, PG 82-16, PG 76-28, PG 76-22, PG 76-16, PG 70-28, 70-22, 70-16, PG 67-28, PG 67-22, PG 67-16, PG 64-28, PG 64-22, PG 64-16, PG 58-34, PG 58-28, PG 58-22, PG 58-16, PG 52-40, PG 52-34, PG 52-28, PG 52-22, and PG 52-16 according to AASHTO M 320-16, and combinations thereof.

In still further preferred embodiments, the prepared modified asphalt composition has a measured difference between a high-temperature PG grade failure temperature from an original sample of the modified asphalt composition and a high-temperature PG grade failure temperature from an RTFO-aged residue sample of the prepared modified asphalt composition that is less than about 1.5° C. In yet further preferred embodiments, the prepared modified asphalt composition has a measured ΔTc of an RTFO plus 60-hour PAV-aged residue sample of the modified asphalt composition that is between about 2.5° C. and about −5.0° C. In still further preferred embodiments, the prepared modified asphalt compositions has a measured ΔTc of an RTFO plus 40-hour PAV tested aged residue sample of the modified asphalt composition that is between about 2.5° C. and about −3.0° C. In yet further preferred embodiments, the prepared modified asphalt composition has a measured change in BBR failure temperature of an RTFO plus 20-hour PAV-aged residue sample of the modified asphalt composition and an RTFO plus 40-hour PAV-aged residue sample of the modified asphalt composition that is less than about 2.5° C. In yet further preferred embodiments, the method further comprises the step of applying aggregates on top of the modified asphalt composition. In particularly preferred embodiments, the step of applying aggregates is performed after the modified asphalt composition is applied to a roadway surface structure to achieve a hot-applied chip seal. In particularly preferred embodiments, the method further comprises the step of mixing in a conventional asphalt additive selected from the group consisting of hardeners, plastomers, and elastomers including, but not limited to, ethylene vinyl acetate (EVA), vinyl acetate-ethylene (VAE), styrene-butadiene-styrene (SBS), styrene butadiene (SB), styrene-butadiene rubber (SBR), SBR Latex, polychloroprene, isoprene, polybutadiene, acrylic, acrylic copolymers, ground tire rubber (GTR), terpolymers, crumb rubber modifier (CRM), polyphosphoric acid (PPA), natural or synthetic waxes, GILSONITE (also known as uintaite), Trinidad Lake asphalt, and other modifiers that are well-known in the industry and commonly used for the purpose of adding elastomeric properties, strength, and/or "grade-bumping" for asphalt compositions, and any combination of the foregoing.

In yet another aspect, methods of preparing a modified asphalt concrete mixture composition comprising: mixing about 3% to about 10% by weight of a modified asphalt composition with about 90% to about 97% by weight of an aggregate material selected from the group consisting of crushed rock/stone, gravel, granite, limestone, crushed concrete, crushed brick, soil, slag, and sand, and combinations thereof. In some embodiments, the base asphalt further comprises a reclaimed asphalt pavement component or a reclaimed asphalt shingle component. In some preferred embodiments, the modified asphalt concrete composition meets TSR requirements according to AASHTO T-284-14 without the use of anti-strip additives, including, but not limited to, amine-based chemistry, non-amine-based chemistry, and lime treatments.

In a further aspect, methods of preparing a pavement structure comprising applying to a roadway surface structure a modified asphalt composition comprising a base asphalt, an aging resistance additive, and an aggregate that effectively resists aging-related failures are provided. In some embodiments, the modified asphalt composition has a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition that is less than about 5.5° C.

In a still further aspect, methods of preparing a pavement structure comprising applying to a soil, subbase, base, or existing pavement surface a modified asphalt composition comprising a base asphalt, an aging resistance additive, and an aggregate that effectively resists aging-related failures are provided. In some embodiments, the modified asphalt composition has a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition that is less than about 5.5° C.

In yet a still further aspect, methods of preparing a pavement structure comprising applying to a roadway surface structure a modified asphalt composition comprising a base asphalt and an aging resistance additive that effectively resists aging-related failures and applying an aggregate material to the applied modified asphalt composition to create a chip seal are provided. In some embodiments, the modified asphalt composition has a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition that is less than about 5.5° C.

In another aspect, aging resistance additives comprising about 65% to about 80% by weight naphthene aromatics and about 10% to about 30% by weight polar aromatics, wherein the aging resistance additives have having a colloidal index between about 7.0 and about 100, are provided. In some embodiments, the aging resistance additives further comprise less than about 13% by weight saturates and/or up to about 1% by weight iso-octane insoluble asphaltenes.

BRIEF DESCRIPTION OF THE DRAWINGS

Further advantages of the invention will become apparent by reference to the detailed description of preferred embodiments when considered in conjunction with the drawings:

FIG. 1A depicts a non-aged, non-distressed AC pavement. FIG. 1B depicts an aged AC pavement that has experienced surface-initiated distress.

FIG. 5 is a table showing asphalt Performance Grade (PG) standards.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Figure 1A:
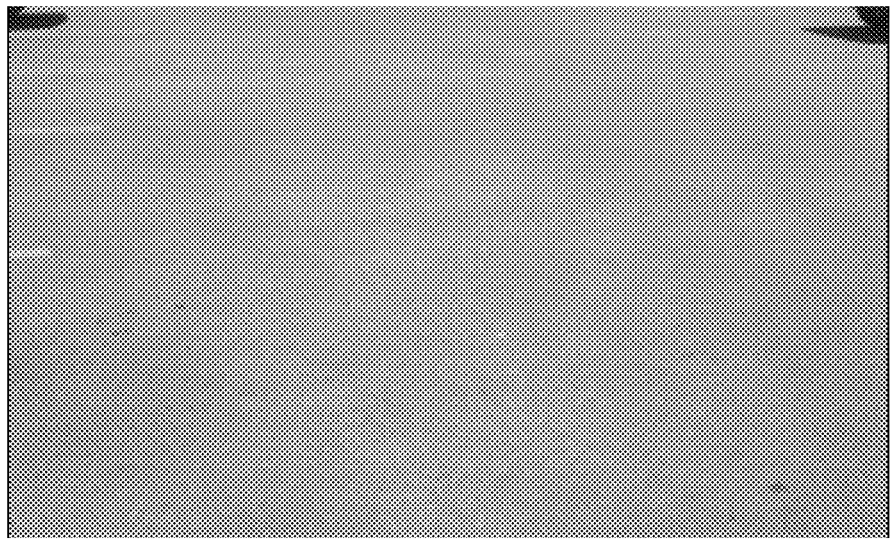
FIGS. 1A-B are representative photographs comparing AC pavement structures with and without surface-initiated distress cracks.
Figure 1B:
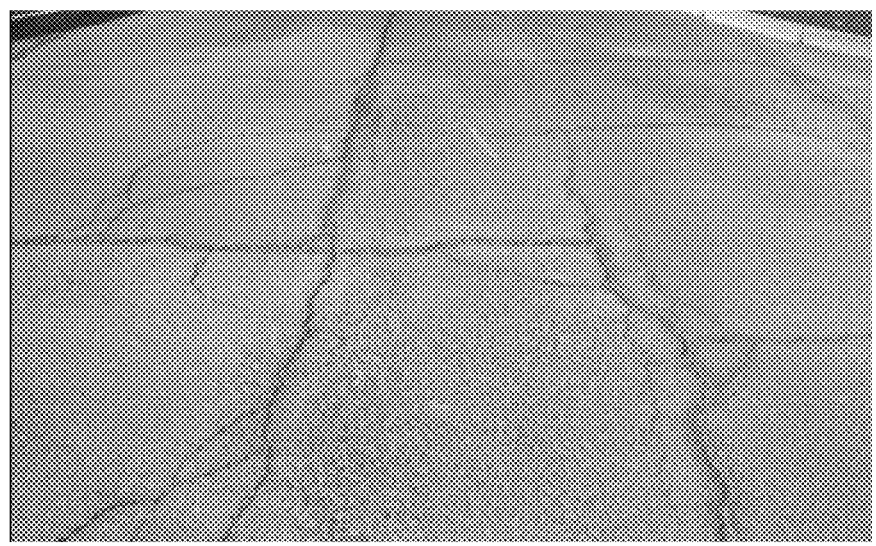

The invention provides several useful embodiments for improving short-term and long-term durability in a variety of asphalt-containing compositions, forms, and products. These asphalt-containing compositions can be used in a variety of road paving applications such as asphalt concrete ("AC") pavement. FIG. 1A depicts a recently constructed typical non-aged, non-distressed AC pavement. FIG. 1B depicts a typical AC pavement that shows signs of aging effects such as surface-initiated distress that causes failure. In some embodiments, the invention provides compositions and methods for creating an asphalt composition that resists the aging effects shown in FIG. 1B. These age-resistant asphalt compositions can meet or exceed the current premier standards for asphalt pavements and can also provide exceptionally high resistance to short-term and long-term aging-related asphalt failures.

In one aspect, an aging resistance additive composition is provided comprising an oil blend of about 65% to about 80% (preferably about 70% to about 76%) by weight naphthene aromatics, about 12% to about 27% (preferably about 15% to about 22% or most preferably about 16% to about 20%) by weight polar aromatics, and, optionally, about 0% to about 12% (preferably about 2% to about 8%) by weight saturates. Optionally, some embodiments of the aging resistance additive may further comprise less than about 1% (preferably less than about 0.1%) by weight of asphaltenes when the total of naphthene aromatics, polar aromatics, and saturates content is less than 100%. The chemical fractions are determined according to ASTM D 4124-09 or IP 143 followed by IP 469.

The various compositions described herein can be characterized in terms of a Colloidal Index ("CI"). CI is determined by the following equation:

$$CI=((NA+PA)/(S+A))$$

where NA represents the proportion by weight (or weight percent) of naphthene aromatics, PA represents the proportion by weight of polar aromatics, S represents the proportion by weight of saturates, and A represents the proportion by weight of asphaltenes. Thus, it should be appreciated that a CI could potentially approach infinity where S+A=0.

In some embodiments, the CI of the aging resistance additive is greater than about 7 (preferably between about 10 and about 100 and most preferably between about 10 and about 50). In some embodiments, the aging resistance additive has a paraffin wax content, according to European Standard EN 12606 (2015), of less than about 0.5% (preferably less than about 0.2%). Preferably, the aging resistance additive has a Cleveland open cup flash point ("COC") according to AASHTO T 48-06 (2015) between about 200° C. and 300° C. (preferably between about 230° C. and about 290° C.). The aging resistance additive can have a kinematic viscosity at 60° C. according to AASHTO T 201-15 of between about 20 cSt and about 110 cSt (preferably between about 30 cSt and about 80 cSt and most preferably between about 30 cSt and about 60 cSt). Also, the additive can have and a Saybolt Furol viscosity ("SFS") at 25° C. according to AASHTO T 72-10 (2015) between about 50 s and about 300 s (preferably between about 75 s and about 250 s and most preferably between about 75 s and about 200 s).

After a simulated aging process conducted on the aging resistance additive in the rolling thin-film oven ("RTFO") according to AASHTO T 240-13, the mass loss % according to AASHTO T 240-13 is between about 1% and about 3% (preferably between about 1.2% and about 2.8% and most preferably between about 1.5% and about 2.5%), the kinematic viscosity ratio (after AASHTO T 240-13 aging kinematic viscosity result divided by original (before aging) kinematic viscosity result) is less than about 2.0 (preferably less than about 1.8 and most preferably less than about 1.7), and the Viscosity (SFS) ratio (after AASHTO T 240-13 aging SFS result divided by original (before aging) SFS result) is less than about 2 (preferably less than about 1.6 and most preferably less than about 1.5). The aging resistance additive is an oil blend that may be comprised of a single oil blend component or may be the result of combining multiple separate oil blend components that when combined yield the properties described for the aging resistance additive. It should be understood that "component" in this specific context means an oil blend meeting the requirements described above or a combination of more than one oil (or SARA fraction portions) or oil blend(s) that result in an oil blend meeting the requirements described above.

In some prior art compositions in which asphalt is mixed with cracking resistance additive, the high temperature performance grade of the composition is generally within 2° C. of the high temperature performance grade for the asphalt alone and typically within 1° C. In contrast, the disclosed aging resistance additives of the present invention will, in fact, cause considerable change in high temperature PG of the asphalt in which it is blended. At dosages of about 2%, the high temperature PG of the final asphalt will change at least about 3° C. to about 4° C. compared to the asphalt prior to introducing the additive (may be referred to herein as "original" or "base asphalt" or "unmodified asphalt" or "asphalt composition without the aging resistance additive"). At dosages of about 5%, the high temperature PG will change at least about 6° C. to about 10° C. This fundamental difference indicates that the present aging resistance additives are entirely different to prior art cracking resistance additives. Other differences also exist and are provided herein. The disclosed compositions and methods thus provide modified asphalt compositions that are resistant to aging-related failures beyond the alternatives presently available to the road construction industry.

In another aspect, an aging resistant asphalt composition is provided by combining a base asphalt with between about 0.1% and about 20% of an aging resistance additive, by weight. In some embodiments, the base asphalt is an asphalt that comprises about 39% to about 63% (preferably about 42% to about 55%) by weight naphthene aromatics, about 22% to about 46% (preferably 30% to about 42%) by weight polar aromatics, about 1% to about 11% by weight saturates (preferably about 3% to about 8%), and about 3% to about 16% (preferably about 3% to about 12%) by weight asphaltenes. The base asphalt may be a paving grade or non-paving grade asphalt. In some embodiments, the base asphalt is a paving grade asphalt designated as a penetration ("pen") graded asphalt between about 40 dmm to about 220 dmm according to the ASTM 5-13/AASHTO T49-15, an AC-graded asphalt according to ASTM D3381-12 (Tables 2 or 4), an AR-graded asphalt according to ASTM D3381-12 (Table 3), or a premium PG graded asphalt according to AASHTO M 320-16. In other embodiments, the base asphalt is a non-paving grade and non-reclaimed "hard pen asphalt" having, as the term is used herein, a penetration ("pen") value of about 40 dmm or less (preferably between about 25 dmm and about 10 dmm) according to the ASTM 5-13/AASHTO T49-15 standard asphalt tests. Under the meaning used herein, a "hard pen asphalt" also has a measured ring and ball softening point ("SP") greater than about 60° C. (140° F.), and preferably between about 60° C. and about 75° C. (167° F.) according to the AASHTO T53-09 (2013) standard asphalt test.

The base asphalt can be a combination of paving grade asphalt and non-paving grade asphalt as described herein. In some aspects, the base asphalt has a measured difference of less than about 1.5° C. between a high-temperature PG grade failure temperature from an original sample of the asphalt composition and a high-temperature PG grade failure temperature from an RTFO-aged residue sample of the aging resistant asphalt composition (as determined under AASHTO T 240-13). In other aspects, the base asphalt has a measured ΔTc between about 2.5° C. and about −7.0° C. (preferably between about 2.5° C. and about −5.5° C.) for an RTFO (as determined under AASHTO T 240-13) plus a 60-hour pressure-aging vessel (PAV) aged residue sample of the asphalt composition (it should be understood that a 60-hour PAV test includes three consecutive 20-hour PAV cycles according to AASHTO R 28-12 (2016) where the aging temperature and pressure are continuous during the 60-hour test period, and designated aging temperature is commensurate to the climate region as specified in AASHTO M320-16).

In yet further embodiments, the base asphalt has a measured ΔTc between about 2.5° C. and about −4.0° C. for an RTFO (AASHTO T 240-13) plus 40-hour PAV-aged residue sample of the aging resistant asphalt composition (multiple PAV, i.e., two continuous 20-hour, cycles according to AASHTO R 28-12 (2016)). In still yet further embodiments, the base asphalt has a measured change of less than 7° C. between BBR failure temperature of an RTFO (AASHTO T 240-13) plus 20-hour PAV-aged residue sample of the aging resistant asphalt composition (AASHTO R 28-12 (2016)) and an RTFO (AASHTO T 240-13) plus 60-hour PAV-aged residue sample of the asphalt composition (multiple PAV, i.e., three continuous 20-hour, cycles according to AASHTO R 28-12 (2016)). In even further embodiments, the aging resistant asphalt composition has a measured change less than 4.0° C. between BBR failure temperature of an RTFO (AASHTO T 240-13) plus 20-hour PAV-aged residue sample of the asphalt composition (AASHTO R 28-12 (2016)) and an RTFO (AASHTO T 240-13) plus 40-hour PAV-aged residue sample of the asphalt composition (multiple PAV, i.e., two continuous 20-hour, cycles according to AASHTO R 28-12 (2016)).

In some preferred embodiments, the amount of aging resistance additive is preferably less than 5%, with some preferred ranges such as 5% to 2% and 2% to 0.1%. In other preferred embodiments, the amount of aging resistance additive can be greater than 5% and as high as 20%, with some preferred ranges such as 20% to 15%, 15% to 10%, and more preferably 10% to 5% for high dosage applications. In some embodiments, the aging resistant asphalt composition comprises, in total, about 40% to about 60% (preferably about 42% to about 55%) by weight naphthene aromatics, about 25% to about 45% (preferably about 30% to about 42%) by weight polar aromatics, about 1% to about 10% by weight saturates (preferably about 3% to about 8%), and about 3% to about 15% (preferably about 3% to about 12%) by weight asphaltenes. In some embodiments, the aging resistant asphalt composition further comprises a CI of between about 3.7 and about 8.0 (preferably between about 4.0 and about 8.0).

In some embodiments, an aging resistant asphalt composition meets or exceeds the minimum specification requirements for a conventional paving grade asphalt. These conventional paving grade asphalts include penetration ("pen") graded asphalts 40 dmm to 220 dmm according to the ASTM 5-13/AASHTO T49-15, AC-graded asphalts AC-2.5, AC-5, AC-10, AC-20, AC-30, and AC-40 according to ASTM D3381-12 (Table 2 or Table 4 equivalents), AR-graded asphalts AR-1000, AR-2000, AR-4000, AR-8000, and AR-16000 according to ASTM D3381-12, and premium PG grades PG 82-28, PG 82-22, PG 82-16, PG 76-28, PG 76-22, PG 76-16, PG 70-28, 70-22, 70-16, PG 67-28, PG 67-22, PG 67-16, PG 64-28, PG 64-22, PG 64-16, PG 58-34, PG 58-28, PG 58-22, PG 58-16, PG 52-40, PG 52-34, PG 52-28, PG 52-22, and PG 52-16 according to AASHTO M 320-16.

In some embodiments, the aging resistant asphalt composition has a low paraffin wax content of less than about 1.5% by weight according to EN 12606 (2015). In further embodiments, the aging resistant asphalt composition has a measured difference of less than about 1.5° C. (preferably less than about 1.0° C.) between a high-temperature PG grade failure temperature from an original sample of the asphalt composition and a high-temperature PG grade failure temperature from an RTFO-aged residue sample of the aging resistant asphalt composition (as determined under AASHTO T 240-13).

In still further embodiments, the aging resistant asphalt composition has a measured ΔTc between about 2.5° C. and about −4.5° C. (preferably between about 2.5° C. and about −3.0° C.) for an RTFO (as determined under AASHTO T 240-13) plus a 60-hour pressure-aging vessel (PAV) aged residue sample of the asphalt composition. It should be understood that a 60-hour PAV test includes three consecutive 20-hour PAV cycles according to AASHTO R 28-12 (2016) where the aging temperature and pressure are continuous during the 60-hour test period, and designated aging temperature is commensurate to the climate region as specified in AASHTO M320-16.

In yet further embodiments, the aging resistant asphalt composition has a measured ΔTc between about 2.5° C. and about −2.0° C. for an RTFO (AASHTO T 240-13) plus 40-hour PAV-aged residue sample of the aging resistant asphalt composition. It should be understood that the 40-hour PAV-aged residue sample is achieved by two continuous 20-hour, cycles according to AASHTO R 28-12 (2016).

In still yet further embodiments, the aging resistant asphalt composition has a measured change of less than 5° C. between BBR failure temperature of an RTFO (AASHTO T 240-13) plus 20-hour PAV-aged residue sample of the aging resistant asphalt composition (AASHTO R 28-12 (2016)) and an RTFO (AASHTO T 240-13) plus 60-hour PAV-aged residue sample of the asphalt composition (multiple PAV, i.e., three continuous 20-hour, cycles according to AASHTO R 28-12 (2016)).

In even further embodiments, the aging resistant asphalt composition has a measured change less than 2.5° C. between BBR failure temperature of an RTFO (AASHTO T 240-13) plus 20-hour PAV-aged residue sample of the asphalt composition (AASHTO R 28-12 (2016)) and an RTFO (AASHTO T 240-13) plus 40-hour PAV-aged residue sample of the asphalt composition (multiple PAV, i.e., two continuous 20-hour, cycles according to AASHTO R 28-12 (2016)).

In another aspect, a method of preparing an aging resistant asphalt composition is provided comprising mixing an aging resistance additive and an asphalt base. The aging resistance additive can be added to the asphalt base at a percentage ranging from about 0.1% to about 20%. According to some embodiments, the aging resistance additive comprises an oil blend of about 65% to about 80% (preferably about 70% to about 76%) by weight naphthene aromatics, about 12% to about 27% (preferably about 15% to about 22% or most preferably about 16% to about 20%) by weight polar aromatics, and, optionally, about 0% to about 12% (preferably about 2% to about 8%) by weight saturates. Optionally, some embodiments of the aging resistance additive may further comprise less than about 1% (preferably less than about 0.1%) by weight of asphaltenes when the total of naphthene aromatics, polar aromatics, and saturates content is less than 100%. The chemical fractions in these formulations can be determined according to ASTM D 4124-09 or IP 143 followed by IP 469.

In some embodiments of this method, the CI of the aging resistance additive is greater than about 7 (preferably between about 10 and about 100 and most preferably between about 10 and about 50), and the paraffin wax content of the aging resistance additive according to EN 12606 (2015) is less than about 0.5% (preferably less than about 0.2%). The aging resistance additive advantageously has a flash point ("COC") according to AASHTO T 48-06 (2015) between about 200° C. and 300° C. (preferably between about 250° C. and about 290° C.). The kinematic viscosity of the aging resistance additive at 60° C. according to AASHTO T 201-15 can be between about 20 cSt and about 100 cSt (preferably between about 30 cSt and about 80 cSt and most preferably between about 30 cSt and about 60 cSt). The SFS viscosity at 25° C. according to AASHTO T 72-10 (2015) can be between about 50 s and about 300 s (preferably between about 75 s and about 250 s and most preferably between about 75 s and about 200 s).

According to this method, after a simulated aging process conducted on the aging resistance additive in the RTFO according to AASHTO T 240-13, the mass loss % according to AASHTO T 240-13 can be between about 1% and about 3% (preferably between about 1.2% and about 2.8% and most preferably between about 1.5% and about 2.5%). The kinematic viscosity ratio, which is the ratio of the kinematic viscosity of the aging resistance additive after AASHTO T 240-13 aging divided by the kinematic viscosity of the original aging resistance additive before aging, can be less than about 2.0, preferably less than about 1.8, and even more preferably less than about 1.7. Similarly, the SFS viscosity ratio, which is the ratio of the SFS viscosity of the aging resistance additive after AASHTO T 240-13 aging divided by the SFS viscosity of the original aging resistance additive before aging, can be less than about 2, preferably less than about 1.6, and even more preferably less than about 1.5.

The aging resistance additive of this method can be an oil blend that may be comprised of a single oil blend component or may be the result of combining multiple separate oil blend components that when combined yield the properties described for the aging resistance additive. In some embodiments, the base asphalt can be an asphalt that comprises about 39% to about 63% (preferably about 42% to about 55%) by weight naphthene aromatics, about 22% to about 46% (preferably 30% to about 42%) by weight polar aromatics, about 1% to about 11% by weight saturates (preferably about 3% to about 8%), and about 3% to about 16% (preferably about 3% to about 12%) by weight asphaltenes.

The base asphalt according to the method can be a paving grade asphalt or a non-paving grade asphalt. In some embodiments, the base asphalt is a paving grade asphalt designated as a penetration ("pen") graded asphalt between about 40 dmm to about 220 dmm according to the ASTM 5-13/AASHTO T49-15, an AC-graded asphalt according to ASTM D3381-12 (Tables 2 or 4), an AR-graded asphalt according to ASTM D3381-12 (Table 3), or a premium PG graded asphalt according to AASHTO M 320-16.

In other embodiments of the method, the base asphalt is a non-paving grade and non-reclaimed hard pen asphalt having a penetration ("pen") value of about 40 dmm or less (preferably between about 25 dmm and about 10 dmm) according to the ASTM 5-13/AASHTO T49-15 standard asphalt tests. The hard pen asphalt also has a measured ring and ball softening point ("SP") greater than about 60° C. and preferably between about 60° C. and about 75° C., according to the ASTM D36/AASHTO T53 standard asphalt tests.

In yet other embodiments of the method, the base asphalt is a combination of paving grade asphalt and non-paving grade asphalt. In some preferred embodiments, the amount of aging resistance additive is less than 5%, with ranges such as 5% to 2% and 2% to 0.1%. In still other embodiments, the amount of aging resistance additive can be greater than 5% and as high as 20%, with ranges such as 20% to 15%, 15% to 10%, and preferably 10% to 5% for high dosage applications. The asphalt base further comprises a CI greater than about 3.4 (preferably between about 3.7 and about 8), when between about 0.1% and about 10% of the aging resistance additive is used. Alternately, the asphalt base comprises a CI of greater than about 3.1 (preferably between about 3.4 and 8), when between about 10% and about 20% of the age resistance additive is used.

In further embodiments the present invention provides a method of preparing an aging resistant asphalt composition comprising mixing an asphalt base with an aging resistance additive to yield an aging resistant asphalt composition that is configured to meet or exceed all AASHTO M 320-16 requirements for specified premium PG asphalt.

In further embodiments, the methods of preparing an aging resistant asphalt composition further comprises a softener, including, but not limited to, flux, re-refined engine oil bottom (REOB), vacuum tower asphalt extended (VTAE), petroleum extract, or other known "cutters" to achieve a lower PG grade or less viscous product.

In still further embodiments, the inventive compositions and the methods of preparing an aging resistant asphalt composition can be enhanced to improve aggregate retention in AC pavement mixtures and/or can be enhanced to resist rutting, bottom-up fatigue cracking, and other distress failures by further adding in or combining with additives/modifiers, particularly hardeners, plastomers, and elastomers including, but not limited to, ethylene vinyl acetate (EVA), vinyl acetate-ethylene (VAE), styrene-butadiene-styrene (SBS), styrene butadiene (SB), styrene-butadiene rubber (SBR), SBR Latex, polychloroprene, isoprene, polybutadiene, acrylic, acrylic copolymers, ground tire rubber (GTR), crumb rubber modifier (CRM), terpolymers, polyphosphoric acid (PPA), natural or synthetic waxes, GILSONITE (also known as uintaite), Trinidad Lake asphalt, and other modifiers that are well-known in the industry and commonly used for the purpose of adding elastomeric properties, strength, and/or "grade-bumping" for asphalt compositions, and any combination of the foregoing. These additives are typically added at less than 20% by weight of asphalt and preferably less than 5% by weight of asphalt.

For example, SBS polymer is one of the most widely used asphalt modifiers in the world, and it is typically added at about 2% to about 4% by weight of the asphalt. Oxidizing treatments, which expose the asphalt to air entrainment, heat, pressure, and/or catalysts, may also be used to add desired stiffness to the asphalt. PPA is a well-known asphalt hardener that is typically used at about 0.5 to about 1.5% by weight asphalt. GTR, on the other hand, may enhance elastomeric properties of asphalt like SBS but is typically used in higher percentages ranging from about 5% to about 20% by weight asphalt. These diverse additives/modifiers/treatments are referred to as "conventional asphalt additives" from this point for brevity, but it should be understood that this term is broader than mere asphalt composition conventional asphalt additives unless otherwise noted. Enhancement by conventional asphalt additives may be performed prior to, during, or after mixing with aggregates, cutback agents, or emulsifying agents. A person of ordinary skill in the art can determine the identity of an acceptable or best conventional asphalt additive for a given composition and/or application and the amount thereof to be added for a given aging resistant asphalt composition based on well-known factors in the field, including characteristics gleaned from standardized testing methods of the base asphalt used and/or mixed aging resistant asphalt composition and/or specific product order requirements from a contracting party.

The aging resistance additive can be added to base asphalts described herein to create numerous asphalt-containing products with improved short-term and long-term asphalt durability. The compositions and methods will greatly improve resistance to age-susceptibility when used in any of the following applications, systems, or combinations. One or more of the aging resistant asphalt composition embodiments described above can be used in a variety of asphalt and asphalt concrete (AC) applications and hot-applied chip seal applications. For example, some embodiments of the aging resistant asphalt composition can be a direct replacement for paving-grade virgin (non-reclaimed) asphalt for the preparation of an aging resistant AC pavement mixture by mixing the aging resistant asphalt composition with aggregate. Aggregate material comprises one or more of the following substances: crushed rock/stone, gravel, granite, limestone, crushed concrete, crushed brick, soil, slag, and sand. Some embodiments of the aging resistant AC pavement mixture typically comprises from about 4% to about 8% by weight of an embodiment of aging resistant asphalt composition and from about 92% to about 96% by weight aggregates and mineral fillers.

Alternatively, reclaimed asphalt pavement (RAP) and/or recycled asphalt shingles (RAS) may be included in some embodiments of the aging resistant AC pavement mixture. RAP and RAS contain aggregates and asphalt binder that replace a certain percentage of the required virgin aggregates and virgin aging resistant asphalt composition. Allowable percentage for RAP and RAS can vary significantly depending on RAP and RAS quality and specifications of the governing agency. In the US, average percentages are currently about 20% RAP and about 0% to about 5% RAS. RAS asphalt is much lower quality (e.g., it is usually stiffer and more brittle) and is therefore much more heavily prohibited. As recycling agent technology improves, the allowable percentages of RAP and RAS are likely to increase. In fact, Japan currently allows an average of about 50% RAP in their AC pavement mixtures. Regardless of the percentage of RAP and/or RAS that is included in the mixture, the overall percentage of total asphalt and aggregates remains within the ranges specified herein. However if, for example, 25% RAP is included in a mixture, the amount of age-resistant asphalt composition for that particular aging resistant AC pavement mixture may be reduced by approximately 25% (the new range for aging resistant asphalt composition then becomes about 3% to about 6%) to make room for the RAP asphalt. The same concept holds true for RAS.

But unlike RAP, which contains approximately the same percentage of asphalt as the range above (4-8%), RAS contains between about 15% to about 25% asphalt. Therefore, as little as 5% RAS may replace as much as 25% of the aging resistant asphalt composition in the aging resistant AC pavement mixture. The precise reduction in aging resistant asphalt composition for mixtures containing RAP and/or RAS is calculated based on the percentage of asphalt in the RAP and RAS, which varies per source. When RAP and RAS asphalt are permitted to replace a significant portion of the aging resistant asphalt composition in the aging resistant AC pavement mixture, careful consideration should be given to the overall performance of the newly prepared aging resistant AC pavement mixture, including aging performance. These embodiments of the invention improve aging resistance of the AC pavement proportional to the amount of virgin asphalt that is replaced by aging resistant asphalt composition. It should be understood that the aging resistant AC pavement mixture can be mixed and compacted to meet or exceed applicable standards for mix designs and volumetrics, including AASHTO T 245-15, AASHTO T 246-10 (2015), AASHTO T 247-10 (2015), AASHTO M 323-13, AASHTO M 325-08 (2012), and AASHTO T324-14.

In addition to the aging-resistance properties, in some embodiments the aging resistant AC pavement mixture is resistant to moisture damage as determined according to AASHTO T283-14. The resistance to moisture damage can reduce the need for hydrated lime (optionally added to the aggregates as a replacement of about 1% of the fine aggregate content) or anti-stripping agents (optionally added to the asphalt at approximately 0.5% by weight asphalt). Thus, some embodiments of the aging resistant AC pavement mixture exclude anti-stripping agents as a conventional asphalt additive component.

In other embodiments, the aging resistant asphalt composition (combined with optional conventional asphalt additives) is heated and sprayed directly onto subgrade, subbase, aggregate base, or existing roadway, and in a subsequent step, aggregate "chips", such as crushed rock/stone, gravel, granite, limestone, crushed concrete, crushed brick, soil, slag, sand, RAP, and RAS or combinations thereof are applied directly on top of the aging resistant asphalt composition to create an aging resistant hot-applied chip seal. The aggregate chips are sometimes pre-coated with aging resistant asphalt composition, although this is not always a requirement as with a standard AC pavement mixtures. After the aging resistant asphalt composition is sprayed, the pre-coated or non-pre-coated aggregates are dropped onto a relatively thick film of aging resistant asphalt composition using a chip spreader. The volume of non-aqueous hot-applied aging resistant asphalt composition that is sprayed can vary from 0.20 gal/sy to 0.50 gal/sy and is determined based on the volume of aggregate cover in the design. The amount of aging resistant asphalt composition is sufficient to provide 20% to 60% embedment (more typically 30% to 40%) of the seated aggregate. Multiple consecutive layers may be applied on top of one another, and the terms single-, double-, and triple bituminous surface treatments are commonly used to describe the specific type of chip seal.

These processes and designs are well known to those of ordinary skill in the art and are presented in great detail in manuals such as the *Seal Coat and Surface Treatment Manual* (Revision May 2010), Texas Department of Transportation.

Measuring Performance of Aging Resistant Asphalt Compositions

The following data comparisons depict a conventional asphalt grade of PG 67-22, which is an intermediate premium PG grade commonly specified in the southeastern U.S. However, the exceptional performance demonstrated by the aging resistant asphalt compositions and methods can be applied to asphalts with a variety of different properties, from a variety of different grading systems, and that are used for a variety of different applications. This includes pen-graded asphalts, AC-graded asphalts, AR-graded asphalts, and PG-graded asphalts shown in FIG. 5 (including intermediate PG grades, such as PG 67-22).

The comparisons between the aging resistant asphalt compositions and the conventional paving asphalts focus on the PG grading system, because it is the premier modern-day system that produces the best asphalts. The aging resistant asphalt compositions meet or exceed applicable "PG+" specifications that may not be displayed in FIG. 5 or specified as part of the AASHTO M320-16 standard method. These may include: multiple stress creep and recovery (MSCR), ductility, force ductility, phase angle, and other "additional criteria" that are primarily added by government transportation agencies to ensure that a certain amount/percentage of a particular polymer or other conventional asphalt additive is included in the asphalt.

Aging Resistant Asphalt Compositions—Premature (Pre-Service) Aging Resistance

As shown in the PG specification of FIG. 5, the DSR-derived result $G^*/\sin \delta$ is obtained from the original (non-aged) asphalt and the RTFO-aged asphalt. The latter result represents the asphalt primarily after volatilization, which occurs during the mixing and laydown process. Since all asphalt must go through the mixing and laydown process, the RTFO result should be the result that matters most. The specification only lists a minimum requirement of 1.00 kPa and 2.20 kPa, respectively, for the original and RTFO-aged asphalt results. One way to view these are as a measurement of stiffness. What these values show is that an original asphalt may undergo an increase in $G^*/\sin \delta$ (stiffness) of roughly 120% during the mixing and laydown process to properly resist rutting once in service. Also, the mass change during the RTFO process is restricted at less than 1.00%, as shown. The mass loss restriction is meant to screen for asphalts that are susceptible to excessive volatilization during the mixing and laydown process—an important part of the specification.

In practice, given a specified high temperature grade of 67° C., original and RTFO-aged asphalt samples would both be tested at 67° C. to ensure that $G^*/\sin \delta$ is greater than 1.00 kPa and 2.20 kPa, respectively, and the samples also tested to ensure that their mass loss is less than 1.00%. If each of these three requirements is met, the asphalt passes this portion of the specification.

However, it has been revealed that asphalts with poor colloidal stability, such as non-aged asphalts with micro-structures known as bee structures, will actually undergo excessive age-hardening processes unrelated to mass loss (volatilization) during the mixing and laydown process, which is simulated during the RTFO-aging process. This results in symptoms of premature aging before the asphalt even makes it into service. Techniques such as atomic force microscopy (AFM) have recently been used to confirm confirmed by, that as asphalt ages, its topographical microstructure develops a well-defined pattern of bee structures. (See Allen (2013), Micro structural Characterization of the Chemo-mechanical Behavior of Asphalt in Terms of Aging and Fatigue Performance Properties. *Doctoral Dissertation*, Texas A&M University, College of Engineering, College Station, Tex.) These bee structures (striated occurrences) can be associated with the onset of premature surface-related distress. According to Allen, bee structure patterns can also be found in certain asphalts that have not experienced extensive aging, where bee structuring occurred more often as the percentage of asphalt saturates chemical fraction increased.

These previous findings by Allen (2013), revealing the formation of micro-scale topographical bee structuring in non-aged asphalts with high saturates content and aged asphalts, corroborate a macro-scale-based theory that suggested that an improper balance between asphaltenes and saturates can cause colloidal instability and poor cracking resistance in asphalt that is indicative of a severely aged asphalt. A lack of chemical balance and reduced compatibility between chemical fractions and various molecules develops naturally in asphalt over time due to oxidation and other aging factors. Saturates are typically inert and remain stable over time, but Napthene aromatics convert to polar aromatics, and polar aromatics convert to asphaltenes. Therefore, the ratio of chemical fractions and the colloidal index are always changing with respect to time and exposure to the elements. A key to asphalt aging resistance is maintaining better balance over longer periods of time. Controlling the chemical fractions of the asphalt prior to aging (virgin asphalt) is not the only variable that matters, but controlling this variable can be important to overcoming aging susceptibility. Additionally, various physical characteristics of the asphalt should preferably be present. These can typically be determined via laboratory aging simulation combined with various DSR and BBR testing protocols described herein. Combining these theories and microstructural studies with a thorough investigation into the known chemical and physical age-susceptibility of asphalts that are aged and tested beyond typical required aging simulations can assist in determining why even so-called high quality asphalts routinely experience premature surface-initiated distress.

SARA and colloidal stability related variables can assist in distinguishing between base asphalts/final blended asphalts that have a chance of resisting aging versus asphalts that have a low probability of resisting aging. Although, even some asphalts with high colloidal stability will still experience similar premature (and even long-term) aging affects, so proper screening must be implemented to ensure that both high colloidal stability and resistance to aging according to various test procedures are present in the base asphalt prior to blending with the described age-resistant additive as well as the final asphalt composition to be used after blending. This effect of premature aging can be measured by performing a continuous grading (actual failing temperature) on an original asphalt and on an RTFO-aged asphalt.

In a continuous grading scheme, if both original and RTFO samples are tested at 67 C, and result in measurements of exactly 1.00 kPa and 2.20 kPa, the failing temperature for the original and RTFO-aged sample would both be exactly 67° C. in both cases. However if, for example, the original asphalt failed at exactly 1.00 kPa and the RTFO sample failed at 4.5 kPa (instead of 2.20 kPa), the failure temperature for the original sample was 67° C., but the failure temperature for the RTFO-aged asphalt was likely a higher grade—let's say 71. This increase above and beyond 2.20 kPa signifies premature aging that has occurred (and will likely continue to occur while in service), resulting in excessive hardening of the asphalt. Nonetheless, the sample still "passes" as long as the mass loss is restricted at less than 1.00%. It should be understood that there are cases of asphalts that do not show premature aging susceptibility in short-term aging analysis, as explained here, but show extreme sensitivity to long-term aging. A truly age-resistant composition displays characteristics of both short-term and long-term aging resistance. The following section and Examples section provides details which explain and further differentiate the two.

Aging Resistant Asphalt Compositions—Long-Term (in-Service) Aging Resistance

It has been stated that inherent flaws and poor aging resistance in even the highest quality asphalts have limited specifications, long-term aging predictions, and performance in asphalt products. Although AASHTO M320-16 does not currently specify sufficiently long-term aging resistance in asphalts, innovation that leads to improved asphalt aging resistance requires that this type of investigation to occur. Due to the widespread nature of reported premature surface-initiated cracking failures, researchers have employed state of the art methods to detect potential flaws in asphalts that are presently approved as premium asphalts. As with any new or experimental method, a correlation to field performance is ultimately required to establish credibility and ultimately create a pathway to use the method as a reliable engineering tool. One method that most strongly correlates to pavement distress is known as the Delta Temperature Critical ($\Delta T_c$) test. Although following AASHTO M320-16 provides the necessary data to compute $\Delta T_c$, it has not typically been required by specification (or reported) prior to being introduced to the industry by Anderson et al. (2011) *Evaluation of the Relationship between Asphalt Binder Properties and Non-Load Related Cracking*. Association of Asphalt Paving Technologists. Vol 80, pp. 615-661. Due to the fact that the value is readily available in the data and shows strong correlation to pavement distress, it has since gained widespread acceptance and usage in the industry. In fact, Asphalt Institute (AI) relied heavily on $\Delta T_c$ in the December 2015 publication *State-of-The-Knowledge—The Use of REOB/VTAE in Asphalt*. It was presented in this report that these additives (REOB/VTAE) may reduce $\Delta T_c$, and therefore, reduce aging and cracking performance. According to the report, $\Delta Tc$ is a reliable indicator of when binders are losing the ability to relax stresses and therefore losing the ability to resist crack formation.

As presented earlier in FIG. 5, notice that AASHTO M320-16 requires measurement of S (creep stiffness) and m-value (rate of relaxation) at 60 sec. It is standard that one of these two values controls and defines the low-temperature PG grade; the other value is typically discarded or ignored. For the majority of aged asphalts m-value controls. $\Delta T_c$ is the difference between the continuous S failure temperature and the m-value failure temperature. The further that the two values are apart, the greater the susceptibility of asphalt to age-related, surface-initiated distress. Capturing the value under the standard (7-year) aging simulation provides some value, but the true test is extending the PAV aging from 20 hours to 60 hours to simulate a much higher degree of aging—conceivably approximately 21 years in service (each additional 20-hour PAV test cycle after the first simulating 7 years in-service aging). Continuous multiples of the PAV 20-hour testing period has previously been used by the Asphalt Institute to study the long-term aging susceptibility of asphalts containing REOB. Anderson et al. (2011) recommended a cracking warning limit ($\Delta T_c$) of −2.5° C. and a cracking initiation/acceleration limit of −5.0° C.

Asphalt binder ductility, measured in accordance with ASTM D 113-07, was a common performance measure utilized to assess the cracking susceptibility of the pavement structures. See, e.g., Kandhal and Wenger (1975), Asphalt properties in relation to pavement performance, Transportation Research Record, 544:1-13, and Kandhal and Koelher (1984), Significant studies on asphalt durability: Pennsylvania experience, Transportation Research Record, 999:41-50, established that the binder ductility at 15.6° C. best correlated to the cracking performance of the pavements after 10 years. Kandhal (1977), Low-Temperature Ductility in Relation to Pavement Performance", ASTM STP 628: Low-Temperature Properties of Bituminous Materials and Compacted Bituminous Paving Mixtures, C. R. Marek (Ed.), American Society for Testing and Materials, Philadelphia, Pa., developed associated performance thresholds wherein a ductility value of 5 cm indicated the onset of cracking and a ductility value of 3 cm indicated extensive cracking in the pavements requiring resurfacing. Although ductility can be a reliable predictor of binder aging, the method required to determine ductility of aged binder specimens is tedious and time-intensive. This had led researches to develop less tedious parameters which correlate to ductility of aged binders.

A more convenient parameter that correlates to the ductility of aged binders is the Glover-Rowe ("G-R") parameter. Determining the G-R parameter requires more technical expertise to understand (compared to ductility and $\Delta T_c$), but once the method is understood, it can be a relatively fast, easy, repeatable, and reliable binder aging performance indicator. Ruan et al. (2003), An investigation of asphalt durability: Relationships between ductility and rheological properties for unmodified asphalts. Petroleum Science and Technology, 21(1 & 2), 231-254, successfully developed and correlated the dynamic shear rheometer (DSR) function, G'/(η'/G') (where G' is the storage modulus, and η' is the dynamic viscosity of the binder) measured at 15° C. and 0.005 rad/s to the binder ductility measured at 15° C. and 1 cm/min for conventional unmodified binders at different aging conditions. Rowe, G. (2011). Evaluation of the relationship between asphalt binder properties and non-load related cracking. Prepared discussion. Journal of the Association of Asphalt Paving Technologists, 80, 649-663, later reduced the DSR function to the presently known G-R parameter, as expressed in the following equation.

$$G - R = \frac{|G^*|(\cos \delta)^2}{\sin \delta}$$

where G* is the complex modulus and δ is the phase angle at 15° C. and 0.005 rad/s.

Figure 6:
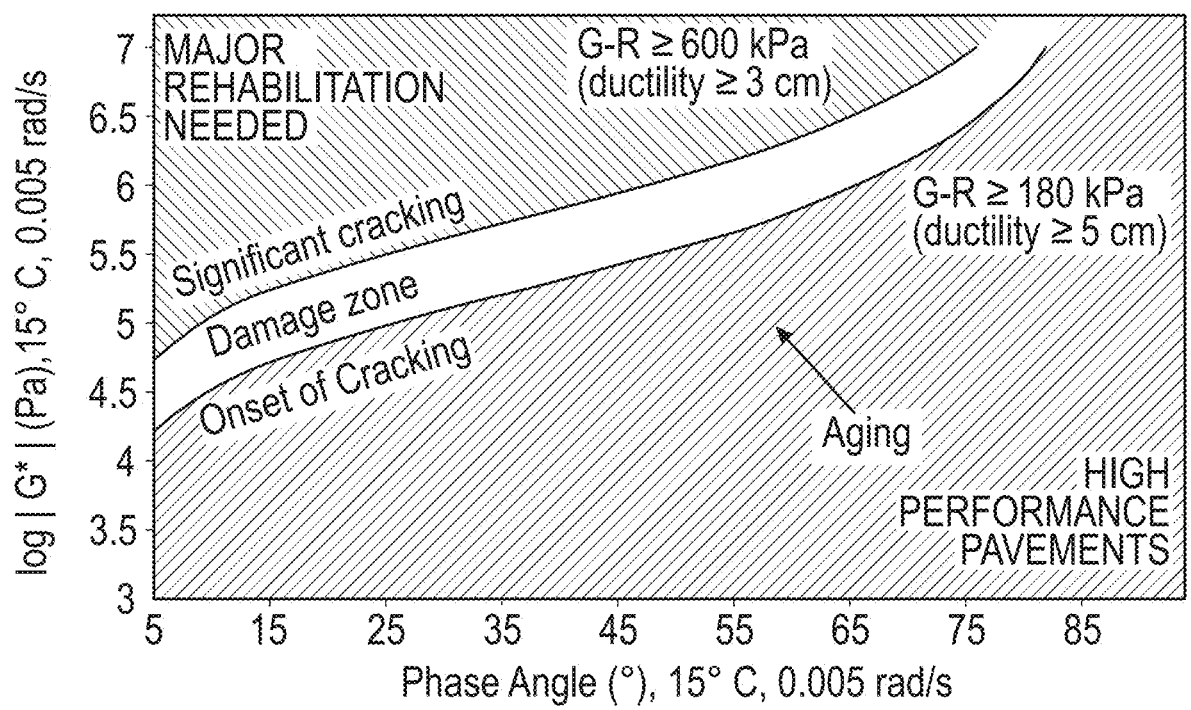
FIG. 6 is an asphalt binder Black Space diagram.

The G-R parameter corresponds to the previously developed ductility thresholds of 5 cm and 3 cm at 180 kPa and 600 kPa respectively. A binder's G-R parameter values at different aging states are typically represented in the form of a Black Space diagram (as shown in the FIG. 6) utilizing the G* and δ values 15° C. and 0.005 rad/s relative to the associated ductility failure planes to illustrate the binder's march to severe embrittlement.

Pavements that resist aging according to this parameter, contain binder with G-R parameter values that remain below the 180 kPa and 600 kPa thresholds for as long as possible. The aging resistant composition and methods described in this invention produce an asphalt binder composition which extends the binder PAV aging hours prior to crossing each of these critical G-R parameter thresholds.

Determination of G-R Parameter:

For the current work, G-R parameter values are determined by utilizing a modified version of the DSR frequency sweep testing originally proposed by Anderson et al. (2011), Evaluation of the relationship between asphalt binder properties and non-load related cracking, Journal of the Association of Asphalt Paving Technologists, 80, 615-663. DSR frequency sweeps from 100 to 0.01 rad/s were performed at 5, 15, and 25° C. at strain levels 0.05, 0.25 and 0.50% respectively using 8-mm parallel geometry with a 2-mm gap at different aging states. The isothermal frequency sweep data obtained at 19 frequencies ramped logarithmically between 100 and 0.1 rad/sec at each aging state considered were fit using Excel™ solver to the commonly used Christensen-Anderson (CA) model (Christensen and Anderson (1992), Interpretation of dynamic mechanical test data for paving grade asphalt, Proceedings of the Association of Asphalt Paving Technologists, 61, 67-116) and a time-temperature superposition as presented in the equations below to develop master curves at a reference temperature of 15° C. and hence determine the G-R parameter at 0.005 rad/s.

$$G^*(\omega_r) = G_g\left[1 + \left(\frac{\omega_c}{\omega_r}\right)^{\frac{\log 2}{R}}\right]^{-\frac{R}{\log 2}}; \quad \delta(\omega_r) = \frac{90}{\left[1 + \left(\frac{\omega_c}{\omega_r}\right)^{\left(\frac{\log 2}{R}\right)}\right]}$$

where $G_g$ is the glassy modulus (assumed a constant value of $10^9$ Pa at different aging stated), $\omega_c$ is the crossover frequency (where phase angle (δ) is 45°), R is the rheological index (determined as the difference between the glassy modulus ($G_g$) and the crossover modulus ($G_c$) i.e. modulus at $\omega_c$), and $\omega_r$ is the reduced frequency determined using the Williams-Landel-Ferry (WLF) equation for time-temperature superposition (Williams et al. (1955), Journal of American Chemical Society, Vol. 77, No. 14, pp. 3701-3707).

$$\omega_r = \omega\alpha(T); \quad \log\alpha(T) = \frac{-C_1(t - T_{ref})}{C_2 + (T - T_{ref})}$$

where ω is angular frequency at which a measurement is performed, α(T) is the time-temperature shift factor to be applied to the measurement at an arbitrary temperature, T to move it to the reference temperature ($T_{ref}$=15° C. for the G-R parameter) at which the master curve is plotted, and $C_1$ and $C_2$ are arbitrary material constants dependent on the material and the reference temperature.

Another parameter, known as crossover temperature (COT), has been used to determine whether a binder has a suitable viscoelastic balance at in-service temperatures to resist distress—particularly surface initiated cracking after the binder has aged. Asphalt binder exhibits viscoelastic response at normal service temperatures. At any given temperature and frequency (or time), in mechanical terms, the binder possesses an elastic response parameter, known as storage modulus (G') and a viscous response parameter, known as loss modulus (G"). The binder behaves solid-like with some viscous response at lower service temperatures (G'>G") and fluid-like with some elastic response (G'<G") at higher service temperatures. The nature of the viscoelastic response is numerically expressed as phase angle (δ) where δ=0° corresponds to purely elastic response, δ=90° corresponds to purely viscous response, and δ=45° corresponds to the point where G'=G" where the binder transitions from solid-like to fluid-like response or vice-versa. The temperature at which G'=G" or δ=45° at a given time or frequency is called the COT ($T_{G'=G"}$). In terms of binder performance, this point can also be viewed as the rheological balance between the rutting and cracking performance at any point in the binder's life cycle. At a given frequency of loading, the magnitude of $T_{G'=G"}$ increases with aging implying that the binder predominantly exhibits elastic or rather brittle (with aging) response at normal service temperatures (more solid-like behavior). The critical distresses that the PG binder specification attempts to preclude at intermediate service temperatures (G*sin δ) and low service temperatures (S and m-value) are fatigue cracking and thermal cracking, respectively. These parameters were specified to ensure that the binder is viscous enough at these temperatures to prevent cracking in pavements. However, a significant increase in $|T_{G'=G''}|$ with aging may provide a more accurate prediction of cracking performance than the aforementioned PG specification parameters. Therefore, it is important to develop and utilize asphalt binders that are more resistant to an increase in COT value with aging. The aging resistant composition and methods described in this invention produce an asphalt binder composition which is more resistant to an increase in COT value with aging.

Determination of Crossover Temperature:

For the current work, COT ($T_{G'=G''}$) is determined at a given aging state utilizing the master curve fit parameters of the G-R DSR frequency sweep test data with $T_{ref}$=15° C. and the following equation.

$$T_{G'=G''} = -\frac{[(\log\frac{\omega_c}{10})(C_2 - T_{ref}) - T_{ref}C_1]}{[C_1 + \log\frac{\omega_c}{10}]}$$

Aging Resistant Asphalt Composition Formulations and Components:

Aging Resistance Additive:

The aging resistance additive is an oil or oil blend comprising about 65% to about 80% (preferably about 70% to about 76%) by weight naphthene aromatics, about 12% to about 27% (preferably about 15% to about 22% or most preferably about 16% to about 20%) by weight polar aromatics, and about 0% to about 12% (preferably about 2% to about 8%) by weight saturates. Optionally, the aging resistance additive may further comprise less than about 1% (preferably less than about 0.1%) by weight of asphaltenes when the total of naphthene aromatics, polar aromatics, and saturates content is less than 100%. The chemical fractions are determined according to ASTM D 4124-09 or IP 143 followed by IP 469. The CI of the aging resistance additive is greater than about 7 (preferably between about 10 and about 100 and most preferably between about 10 and about 50), and the paraffin wax content of the aging resistance additive according to EN 12606 (2015) is less than about 0.5% (preferably less than about 0.2%). The aging resistance additive has a COC flash point according to AASHTO T 48-06 (2015) between about 200° C. and 300° C. (preferably between about 230° C. and about 290° C.), a kinematic viscosity at 60° C. according to AASHTO T 201-15 of between about 20 cSt and about 100 cSt (preferably between about 30 cSt and about 80 cSt and most preferably between about 30 cSt and about 60 cSt), and a SFS viscosity at 25° C. according to AASHTO T 72-10 (2015) between about 50 s and about 300 s (preferably between about 75 s and about 250 s and most preferably between about 75 s and about 200 s). After a simulated aging process conducted on the aging resistance additive in the RTFO according to AASHTO T 240-13, the mass loss % according to AASHTO T 240-13 is between about 1% and about 3% (preferably between about 1.2% and about 2.8% and most preferably between about 1.5% and about 2.5%), the kinematic viscosity ratio is less than about 2.0 (preferably less than about 1.8 and most preferably less than about 1.7), and the SFS Viscosity ratio is less than about 2 (preferably less than about 1.6 and most preferably less than about 1.5). The aging resistance additive may be a single component system or may be the result of combining multiple components that when combined yield the properties described for aging resistance additive. It should be understood that "component" here means an oil blend meeting the requirements described above or a combination of more than one oils (or SARA fraction portions) or oil blend(s) that result in an oil blend meeting the requirements described above.

Asphalt Base:

The asphalt base is an asphalt that comprises about 39% to about 63% (preferably about 42% to about 55%) by weight naphthene aromatics, about 22% to about 46% (preferably 30% to about 42%) by weight polar aromatics, about 1% to about 11% by weight saturates (preferably about 3% to about 8%), and about 3% to about 16% (preferably about 3% to about 12%) by weight asphaltenes. The base asphalt may be a paving grade or non-paving grade asphalt. In various respects, the base asphalt is a paving grade asphalt designated as a penetration ("pen") graded asphalt between about 40 dmm to about 220 dmm according to the ASTM 5-13/AASHTO T49-15, an AC-graded asphalt according to ASTM D3381-12 (Tables 2 or 4), an AR-graded asphalt according to ASTM D3381-12 (Table 3), or a premium PG graded asphalt according to AASHTO M 320-16. In other respects, the base asphalt is a non-paving grade, non-reclaimed hard pen asphalt having a penetration ("pen") value of about 40 dmm or less (preferably between about 25 dmm and about 8 dmm) according to the ASTM 5-13/AASHTO T49-15 standard asphalt tests. The hard pen asphalt also has a measured ring and ball softening point ("SP") greater than about 60° C. (140° F.) (preferably between about 60° C. and about 75° C. (167° F.)) according to the ASTM D36/AASHTO T53 standard asphalt tests. In yet another respect, the base asphalt is a combination of paving grade asphalt and non-paving grade asphalt. In various respects, the amount of aging resistance additive is preferably less than 5%, with ranges such as 5% to 2% and 2% to 0.1%. In other respects, the amount of aging resistance additive can be greater than 5% and as high as 20%, with ranges such as 20% to 15%, 15% to 10%, and preferably 10% to 5% for high dosage applications. The asphalt base further comprises a CI greater than about 3.4 (preferably between about 3.7 and about 8) when between about 0.1% and about 10% of the aging resistance additive is used. Alternately, the asphalt base comprises a CI of greater than about 3.1 (preferably between about 3.4 and 8) when between about 10% and about 20% of the age resistance additive is used.

Conventional Asphalt Additives:

Softener including but not limited to flux, re-refined engine oil bottom (REOB), anti-strip agents, warm mix additives, vacuum tower asphalt extender (VTAE), petroleum extract, solvents, or other known "cutters" to achieve a lower PG grade, make a less viscous product, improve lubricity in a mixture, or reduce temperature requirements. Hardeners, plastomers, and elastomers including but not limited to ethylene vinyl acetate (EVA), vinyl acetate-ethylene (VAE), styrene-butadiene-styrene (SBS), styrene butadiene (SB), styrene-butadiene rubber (SBR), SBR Latex, polychloroprene, isoprene, polybutadiene, acrylic, acrylic copolymers, ground tire rubber (GTR), crumb rubber modifier (CRM), terpolymers, polyphosphoric acid (PPA), natural or synthetic waxes, GILSONITE (also known as uintaite), Trinidad Lake asphalt, and other modifiers that are well-known in the industry and commonly used for the purpose of adding elastomeric properties, strength, and/or "grade-bumping" asphalt compositions, and any combination of the foregoing. As noted above, this optional component is referred to as "conventional asphalt additives." Conventional asphalt additives are optional components of the invention. One or more conventional asphalt additives may be needed to enhance performance (especially to prevent bottom-up fatigue cracking, plastic deformation (rutting)) and/or meet the final product requirements set by a government transportation agency or other entity contracting for a pavement job or a pavement maintenance job. The amount of conventional asphalt additive(s) used may be any amount that is typically used for modifying asphalts for a given application and/or asphalt product. These amounts are well-known in the field. Thus, it should be understood that a person of ordinary skill in the art would be able to determine what conventional asphalt additive(s) and what amount(s) is/are desirable or required to meet a given application condition or contract requirement for the modified asphalt. This optional component is available within the constraints of the minimum testing criteria and properties described herein for the aging resistant asphalt compositions and methods.

Aging Resistant Asphalt Composition Formulation:

The aging resistant asphalt composition formula shall comprise by weight at least: aging resistance additive (about 0.1% to about 20%); base asphalt (about 80% to about 99.9%); modifiers (optional) (about 0% to about 20%; typically <about 5%). The aging resistant asphalt composition formulation is the base formula for all compositions and methods of the invention, with or without the optional component. Modifiers (note 0% content), while a blend of base asphalt and aging resistance additive is required. The foregoing base asphalt composition formulation is then used in each of the following specific application formulations, and therefore, will necessarily be included at less than 100% by weight to create the following compositions and products.

Aging Resistant Asphalt Concrete (AC) Pavement Mixture Formulation:

Embodiments of an aging resistant AC pavement mixture of the present invention can include by weight: aging resistant asphalt composition (about 1% to about 8%) and aggregates/mineral fillers, including hydrated lime or other anti-stripping minerals (about 96% to about 20%). RAP and/or RAS can be included in some embodiments as a portion of the formulation to replace virgin aggregates and virgin age-resistant asphalt composition. The low end of the ranges given above account for up to 75% aggregate and age-resistant asphalt composition replacement by RAP/RAS. The aging resistant AC pavement mixture can be prepared by mixing aging resistant asphalt composition with aggregate using any conventional method or equipment known in the field. Aging resistant AC pavement mixtures may include a variety of lift thicknesses and mix gradations that can be constructed into new pavement or overlay/ultrathin overlay of existing milled/non-milled pavement, including standard AC, hot mix asphalt (HMA), warm mix asphalt (WMA), dense-graded mixtures, open-graded friction course (OGFC), permeable/porous friction course (PFC), stone matrix/mastic asphalt (SMA), and thin overlay mixes (TOM). These and other lift thicknesses and mix gradations are well-known in the field, and any known AC mixing method and/or equipment can be used to prepare the aging resistant AC pavement. Typically, the aging resistant asphalt composition is heated to a liquid/pourable state at about 300° F. to about 400° F. before mixing with the aggregate.

It is also typical that the aggregate is heated prior to mixing, to prevent rapid cooling of the asphalt binder and which may also be advantageous for removing any residual water that could be held by the aggregate material.

Advantages for Reclaimed Asphalt Pavements

The present aging resistant asphalt composition yields extreme durability against the elements for all pavement types and provides a much-needed tool for engineers to design roadways of the future. Another important consideration relative to the aging resistant asphalt composition applies to its use in RAP. The reality is that even an aging resistant asphalt composition will eventually experience an end-of-life event—possibly due to load-related failure rather than aging-related failures that are most common. When it does fail and becomes RAP, the quality of the asphalt in the RAP that is added back as a % (typically up to 20% or more) into a new AC pavement mixture will be a much higher quality and less brittle than what is being reused today. This means that the aging resistant asphalt compositions will continue to have a measurable impact even well-beyond its useful service life, as it is re-implemented into the next generation of roadways via the RAP process.

Aging Resistant Hot-Applied Chip Seal Formulation:

The aging resistant hot-applied chip seal formula shall comprise by weight at least: aging resistant asphalt composition (about 0.5% to about 8%) and aggregates (about 99.5% to about 92%). The aging resistant asphalt composition (combined with optional conventional asphalt additives) is heated and sprayed directly onto an aggregate base, subbase, or existing roadway, and in a subsequent step, aggregate "chips", such as crushed rock/stone, gravel, granite, limestone, crushed concrete, crushed brick, soil, slag, sand, RAP, and RAS or combinations thereof are applied directly on top of the aging resistant asphalt composition to create an aging resistant hot-applied chip seal. The aggregate chips are sometimes pre-coated with aging resistant asphalt composition, although this is not always a requirement as with a standard AC pavement mixtures. After the aging resistant asphalt composition is sprayed, the pre-coated or non-pre-coated aggregates are dropped onto a relatively thick film of aging resistant asphalt composition. Shortly after, the chip-covered surface is ready for traffic. The volume of non-aqueous hot-applied aging resistant asphalt composition that is sprayed to hold the chips in place can vary from 0.20 gal/sy to 0.50 gal/sy and is determined based on the volume of aggregate cover in the design. The amount of aging resistant asphalt composition is sufficient to provide 20% to 75% embedment (more typically 30% to 40% initial embedment) of the seated aggregate chips. Multiple consecutive layers may be applied on top of one another. These processes and designs are well known to those of ordinary skill in the art and are presented in greater detail in manuals such as the *Seal Coat and Surface Treatment Manual* (Revision May 2010), Texas Department of Transportation.

EXAMPLES

Various aspects of the invention will now be discussed with the aid of exemplary embodiments and examples. These exemplary embodiments and examples are non-limiting, and, as such, are provided for illustration of some of the useful and novel properties and characteristics of the invention in these forms. A person of ordinary skill in the art will understand from the following description that the inventive compositions and methods can be applied to other asphalt compositions and methods that will and are contemplated to be within the scope of the invention.

Example 1—Aging Resistance Additive

Below are presented TABLES 2 to 5, which provide general properties of the additive and Examples 1-3, 1-4, and 1-5, respectively, of exemplary embodiments of the Aging Resistance Additive. The additive or combination of additives may be selected from the group consisting of petroleum extracts, bio-derived additives, synthetically-derived additives, and various other oils or combinations of oils as long as the properties exhibit those described.

TABLE 2

General Chemical and Physical Properties of Aging Resistance Additive

| PARAMETER | TEST METHOD | MIN | MAX |
|---|---|---|---|
| Chemical Properties | | | |
| Naphthene Aromatics, % | ASTM D 4124 or | 65.0 | 78.0 |
| Polar Aromatics (Resins), % | IP 143 followed by | 12.0 | 27.0 |
| Saturates, % | IP 469 | 1 | 12.0 |
| Asphaltenes, % | | 0 | 1.0 |
| Colloidal Index (CI) = ((NA + PA)/(S + A)) | N/A | 7.0 | — |
| Paraffin Wax content, % | EN 12606 | 0 | 0.5 |
| Physical Properties (Original Additive/Before Aging) | | | |
| Flash Point (Cleveland Open Cup), ° C. | AASHTO T 48 | 200.0 | 300.0 |
| Kinematic Viscosity @ 60° C., cSt | AASHTO T 201 | 20.0 | 100.0 |
| Saybolt Furol Viscosity (SFS) @ 25° C., s | AASHTO T 72 | 50.0 | 300.0 |
| Physical Properties (RTFO residue/After aging according to AASHTO T 240) | | | |
| Mass Loss, % | AASHTO T 240 | 1.0 | 3.0 |
| Kinematic Viscosity ratio (after/before aging) | AASHTO T 201 | 0 | 2.0 |
| SFS Viscosity ratio (after/before aging) | AASHTO T 72 | 0 | 2.0 |

TABLE 3

Chemical and Physical Properties of a Preferred Aging Resistance Additive Example 1-3

| PARAMETER | TEST METHOD | RESULT |
|---|---|---|
| Chemical Properties | | |
| Naphthene Aromatics, % | ASTM D 4124 or | 75.5 |
| Polar Aromatics (Resins), % | IP 143 followed by | 18.0 |
| Saturates, % | IP 469 | 6.5 |
| Asphaltenes, % | | 0 |
| Colloidal Index (CI) = ((NA + PA)/(S + A)) | N/A | 14.4 |
| Paraffin Wax content, % | EN 12606 | <0.10 |
| Physical Properties (Original Additive/Before Aging) | | |
| Flash Point (Cleveland Open Cup), ° C. | AASHTO T 48 | 252.0 |
| Kinematic Viscosity @ 60° C., cSt | AASHTO T 201 | 43.0 |
| Saybolt Furol Viscosity (SFS) @ 25° C., s | AASHTO T 72 | 137.0 |
| Physical Properties (RTFO residue/After aging according to AASHTO T 240) | | |
| Mass Loss, % | AASHTO T 240 | −2.2 |
| Kinematic Viscosity ratio (after/before aging) | AASHTO T 201 | 1.5 |
| SFS Viscosity ratio (after/before aging) | AASHTO T 72 | 1.3 |

TABLE 4

Chemical and Physical Properties of a Preferred Aging Resistance Additive Example 1-4

| PARAMETER | TEST METHOD | RESULT |
|---|---|---|
| Chemical Properties | | |
| Naphthene Aromatics, % | ASTM D 4124 or | 74.6 |
| Polar Aromatics (Resins), % | IP 143 followed by | 22.8 |
| Saturates, % | IP 469 | 2.7 |

TABLE 4-continued

Chemical and Physical Properties of a Preferred Aging Resistance Additive Example 1-4

| PARAMETER | TEST METHOD | RESULT |
|---|---|---|
| Asphaltenes, % | | 0 |
| Colloidal Index (CI) = ((NA + PA)/(S + A)) | N/A | 36.3 |
| Paraffin Wax content, % | EN 12606 | <0.10 |
| Physical Properties (Original Additive/Before Aging) | | |
| Flash Point (Cleveland Open Cup), ° C. | AASHTO T 48 | 261.0 |
| Kinematic Viscosity @ 60° C., cSt | AASHTO T 201 | 28.8 |
| Saybolt Furol Viscosity (SFS) @ 25° C., s | AASHTO T 72 | 89.0 |
| Physical Properties (RTFO residue/After aging according to AASHTO T 240) | | |
| Mass Loss, % | AASHTO T 240 | −2.3 |
| Kinematic Viscosity ratio (after/before aging) | AASHTO T 201 | 1.6 |
| SFS Viscosity ratio (after/before aging) | AASHTO T 72 | 1.4 |

TABLE 5

Chemical and Physical Properties of an Aging Resistance Additive Example 1-5

| PARAMETER | TEST METHOD | RESULT |
|---|---|---|
| Chemical Properties | | |
| Naphthene Aromatics, % | ASTM D 4124 or | 76.1 |
| Polar Aromatics (Resins), % | IP 143 followed by | 14.8 |
| Saturates, % | IP 469 | 9.1 |
| Asphaltenes, % | | 0 |
| Colloidal Index (CI) = ((NA + PA)/(S + A)) | N/A | 10.0 |
| Paraffin Wax content, % | EN 12606 | <0.10 |
| Physical Properties (Original Additive/Before Aging) | | |
| Flash Point (Cleveland Open Cup), ° C. | AASHTO T 48 | 244.0 |
| Kinematic Viscosity @ 60° C., cSt | AASHTO T 201 | 73.4 |
| Saybolt Furol Viscosity (SFS) @ 25° C., s | AASHTO T 72 | 247.0 |
| Physical Properties (RTFO residue/After aging according to AASHTO T 240) | | |
| Mass Loss, % | AASHTO T 240 | −2.1 |
| Kinematic Viscosity ratio (after/before aging) | AASHTO T 201 | 1.2 |
| SFS Viscosity ratio (after/before aging) | AASHTO T 72 | 1.2 |

Example 2—Base Asphalt

Below are presented TABLES 6-10, which provide Examples 2-7, 2-8, 2-9, and 2-10, respectively, of exemplary embodiments of the Base Asphalt. Table 6 gives a broad range of possible grades from which the base may be selected and the recommended properties for each grade to optimize the chance of selecting a suitable Base Asphalt to practice the invention. Tables 7-9 (Examples 2-7, 2-8, and 2-9) give examples and properties recommended for certain asphalt grades. Finally, Table 10 (Example 2-10) shows an example where multiple grades were combined together to create the Base Asphalt. Note that if a single asphalt is used as the Base Asphalt and combined with the Aging Resistance Additive, the properties shown in Tables 6-9 are recommended to optimize the chance of selecting a suitable Base Asphalt to make the claimed aging resistant composition. However, if multiple asphalts are blended together to create a Base Asphalt, the properties shown in Tables 6-9 are not necessarily required for each of the asphalts that are combined. Some may have these properties and some may not. However, if the composite of the blended asphalts generally exhibit properties shown in Table 10, for example, the chance of selecting a suitable aging resistance base is significantly improved.

TABLE 6

General Chemical and Physical Properties of a Base Asphalt

| PARAMETER | TEST METHOD | MIN | MAX |
|---|---|---|---|
| Chemical properties | | | |
| Naphthene Aromatics | ASTM D 4124 | 39.0 | 63.0 |
| Polar Aromatics (Resins) | or IP 143 | 22.0 | 46.0 |
| Saturates | followed by IP | 1.0 | 11.0 |

TABLE 6-continued

General Chemical and Physical Properties of a Base Asphalt

| PARAMETER | TEST METHOD | MIN | MAX |
|---|---|---|---|
| Asphaltenes | 469 | 8.0 | 16.0 |
| Colloidal Index (CI) = ((NA + PA)/(S + A)) | N/A | 3.1 | 10.0 |
| Physical Properties (Original Asphalt) | | | |
| Penetration, dmm | AASHTO T 49 | 8.0 | 150.0 |
| Softening Point, ° C. | AASHTO T 53 | 35.0 | 75.0 |
| Physical (Aging-specific Properties) AASHTO T 240-13 and AASHTO R 28 | | | |
| Δ Failure Temp, ° C., G*/SIN (RTFO-Original) | AASHTO T 315 | — | 1.5 |
| Δ BBR Failure Temp, ° C. (RTFO + 40-hr PAV) − (RTFO + 20-hr PAV) | AASHTO T 313 | — | 4.0 |
| Δ BBR Failure Temp, ° C. (RTFO + 60-hr PAV) − (RTFO + 20-hr PAV) | | — | 7.0 |
| Δ Tc, ° C. (RTFO + 40-hr PAV) | | −4.0 | — |
| Δ Tc, ° C. (RTFO + 60-hr PAV) | | −7.0 | — |

TABLE 7

Chemical and Physical Properties of a Preferred Paving Grade Base Asphalt Example 2-7

| PARAMETER | TEST METHOD | RESULT |
|---|---|---|
| Naphthene Aromatics | ASTM D 4124 or | 48.3 |
| Polar Aromatics (Resins) | IP 143 followed by | 31.7 |
| Saturates | IP 469 | 7.3 |
| Asphaltenes | | 12.8 |
| Colloidal Index (CI) = ((NA + PA)/(S + A)) | N/A | 4.0 |
| Physical Properties (Original Asphalt) | | |
| Penetration, dmm | AASHTO T 49 | 57.0 |
| Softening Point, ° C. | AASHTO T 53 | 50.0 |
| PG Grade | AASHTO M320 | PG 67-22 |
| Physical (Aging-specific Properties) AASHTO T 240-13 and AASHTO R 28 | | |
| Δ Failure Temp, ° C., G*/SIN (RTFO-Original) | AASHTO T 315 | 1.5 |
| Δ BBR Failure Temp, ° C. (RTFO + 40-hr PAV) − (RTFO + 20-hr PAV) | AASHTO T 313 | 4.0 |
| Δ BBR Failure Temp, ° C. (RTFO + 60-hr PAV) − (RTFO + 20-hr PAV) | | 7.0 |
| Δ Tc, ° C. (RTFO + 40-hr PAV) | | −4.0 |
| Δ Tc, ° C. (RTFO + 60-hr PAV) | | −7.0 |

TABLE 8

Chemical and Physical Properties of a Preferred Paving Grade Base Asphalt Example 2-8, typically used in a moderately cool climate

| PARAMETER | TEST METHOD | RESULT |
|---|---|---|
| Naphthene Aromatics | ASTM D 4124 or | 50.5 |
| Polar Aromatics (Resins) | IP 143 followed by | 30.6 |
| Saturates | IP 469 | 7.2 |
| Asphaltenes | | 11.8 |
| Colloidal Index (CI) = ((NA + PA)/(S + A)) | N/A | 4.8 |
| Physical Properties (Original Asphalt) | | |
| Penetration, dmm | AASHTO T 49 | 147 |
| Softening Point, ° C. | AASHTO T 53 | 38.0 |
| PG Grade | AASHTO M320 | PG 52-28 |
| Physical (Aging-specific Properties) AASHTO T 240-13 and AASHTO R 28 | | |
| Δ Failure Temp, ° C., G*/SIN (RTFO-Original) | AASHTO T 315 | 1.5 |
| Δ BBR Failure Temp, ° C. (RTFO + 40-hr PAV) − (RTFO + 20-hr PAV) | AASHTO T 313 | 4.0 |
| Δ BBR Failure Temp, ° C. (RTFO + 60-hr PAV) − (RTFO + 20-hr PAV) | | 7.0 |
| Δ Tc, ° C. (RTFO + 40-hr PAV) | | −4.0 |
| Δ Tc, ° C. (RTFO + 60-hr PAV) | | −7.0 |

TABLE 9

Chemical and Physical Properties of a Preferred Non-Paving Grade Hard Pen Base Asphalt Example 2-9, a non-paving grade and non-reclaimed hard pen asphalt

| PARAMETER | TEST METHOD | RESULT |
|---|---|---|
| Naphthene Aromatics | ASTM D 4124 or | 47.9 |
| Polar Aromatics (Resins) | IP 143 followed by | 38.0 |
| Saturates | IP 469 | 2.6 |
| Asphaltenes | | 11.5 |
| Colloidal Index (CI) = ((NA + PA)/(S + A)) | N/A | 6.1 |
| Physical Properties (Original Asphalt) | | |
| Penetration, dmm | AASHTO T 49 | 10.0 |
| Softening Point, ° C. | AASHTO T 53 | 64.0 |
| PG Grade | AASHTO M320 | PG 88-4 |
| Physical (Aging-specific Properties) AASHTO T 240-13 and AASHTO R 28 | | |
| Δ Failure Temp, ° C., G*/SIN (RTFO-Original) | AASHTO T 315 | −1.7 |

TABLE 10

Chemical and Physical Properties of a Preferred Non-Paving Grade plus Paving Grade Base Asphalt Example 2-10, a combination of non-paving grade, non-reclaimed hard pen asphalt, and paving grade asphalt

| PARAMETER | TEST METHOD | RESULT |
|---|---|---|
| Naphthene Aromatics | ASTM D 4124 or | 48.1 |
| Polar Aromatics (Resins) | IP 143 followed by | 34.9 |
| Saturates | IP 469 | 5.0 |

TABLE 10-continued

Chemical and Physical Properties of a Preferred Non-Paving Grade plus Paving Grade Base Asphalt Example 2-10, a combination of non-paving grade, non-reclaimed hard pen asphalt, and paving grade asphalt

| PARAMETER | TEST METHOD | RESULT |
|---|---|---|
| Asphaltenes | | 12.2 |
| Colloidal Index (CI) = ((NA + PA)/ (S + A)) | N/A | 4.9 |
| Physical Properties (Original Asphalt) | | |
| Penetration, dmm | AASHTO T 49 | 34 |
| Softening Point, ° C. | AASHTO T 53 | 57 |
| PG Grade | AASHTO M320 | PG 82-10 |
| Physical (Aging-specific Properties) AASHTO T 240-13 and AASHTO R 28 | | |
| Δ Failure Temp, ° C., G*/SIN (RTFO-Original) | AASHTO T 315 | −0.5 |
| Δ BBR Failure Temp, ° C. (RTFO + 40-hr PAV) − (RTFO + 20-hr PAV) | AASHTO T 313 | 4.0 |
| Δ BBR Failure Temp, ° C. (RTFO + 60-hr PAV) − (RTFO + 20-hr PAV) | | 7.0 |
| Δ Tc, ° C. (RTFO + 40-hr PAV) | | −4.0 |
| Δ Tc, ° C. (RTFO + 60-hr PAV) | | −5.0 |

Please note that the chemical and aging-specific properties described in Tables 7-10 may not be common to any particular source material. It is understood that crude sources and refining processes are constantly changing, sometimes within the span of months and even within the span of weeks or days. For example, the PG 67-22 asphalt shown in Table 7 was provided by a particular asphalt supplier and within a few weeks, the same asphalt (according to PG grade) from the same supplier (but from a different batch or lot), no longer possessed the properties shown in Table 7. Similarly, the hard pen asphalt shown in Table 9 was provided by a particular asphalt supplier and within a few months, a similar asphalt (according to pen and SP) from the same supplier (but from a different batch), no longer possessed the chemical and aging-specific properties shown in Table 9. A person skilled in the art of selecting asphalts will be able to screen asphalts for the required properties that have been described to replicate the invention.

Example 3—Aging Resistant Asphalt Compositions—Short-Term Aging Effects (Examples 3A, 3B, 3C, and 3D)

Figure 2:
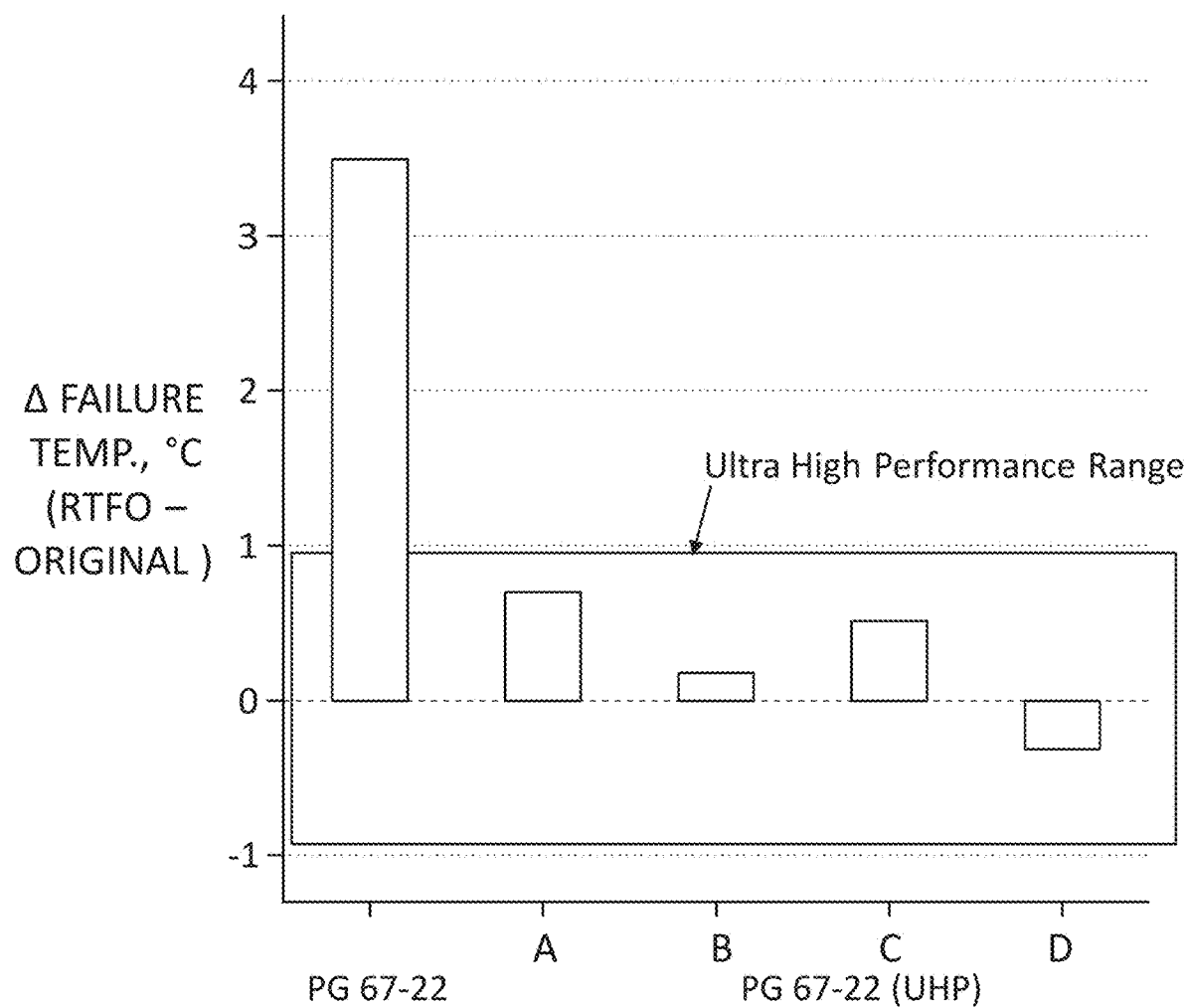
FIG. 2 is a bar graph comparing the susceptibility to premature aging (expressed in terms of Δ Failure Temperature increased high-temperature PG grade after RTFO test aging) between a conventional, PG 67-22 asphalt and four exemplary aging resistant asphalt composition formulations of the present invention.

FIG. 2 is a bar graph showing Δ Failure Temperature (° C.) (defined as difference in high temperature failing grade of an "original sample" and after RTFO aging following AASHTO T240-13) of five samples. The far left bar is a "PG 67-22" sample meeting all requirements of AASHTO M 320-16, which is understood by the industry to produce the most premium asphalt. PG 67-22 has a Δ Failure Temperature of 3.5° C.; to the right are samples (3A-3D), denoted as "PG 67-22 (UHP, (Ultra High Performance))" are each exemplary, independent embodiments of the age-resistant AC composition invention meeting the criteria of PG 67-22 asphalt and age-resistant asphalt composition. Four exemplary embodiments of the invention, 3A, 3B, 3C, and 3D, have Δ Failure Temperatures of 0.7° C., 0.2° C., 0.5° C., and minus (−) 0.31° C., respectively. The Δ Failure Temperature "Ultra High Performance Range" of less than 1.0° C. is denoted with the box on the graph.

FIG. 2, depicts a comparison of the susceptibility to premature aging (expressed in terms of increased high-temperature PG grade after RTFO test aging) between a conventional, premium PG-graded asphalt (labeled as "PG 67-22") and four Example 3 formulations of the aging resistant asphalt composition (labeled as "PG 67-22 (UHP)" and "3A" to "3D"). As shown, the "premium" PG-graded asphalt experienced a true grade increase of 3.5° C., which represents a substantial amount of premature aging, while maintaining a mass loss % of less than 1.00. The original (non-aged) high temperature true grade for this asphalt was 68.1° C. and the RTFO-aged true grade was 71.6° C. These are the specific temperatures at which the 1.00 kPa and 2.20 kPa minimum requirements were met. In comparison, four separate formulations 3A to 3D of the aging resistant asphalt composition were tested under the same conditions, and true grade increases only ranged from −0.31° C. to 0.70° C. The original (non-aged) high temperature true grades were 69.1° C., 69.9° C., 69.1° C., and 69.8° C.; the respective RTFO-aged true grades were 69.8° C., 70.1° C., 69.6° C., and 69.5° C. Each of these five asphalts meet the same grade, but the conventional PG 67-22 asphalt experienced an average of 1,300% more premature age-hardening than the aging resistant asphalt composition samples, PG 67-22 (UHP) A-D. The mass loss %'s for the 5 asphalts were all similar and well-within limits, ranging from −0.20 to −0.30%. Bear in mind that premature aging relative to Δ Failure temperature (or Δ PG grade increase) simulates aging that occurs before the pavement is even opened to traffic. The final RTFO grade should not be the focus of this analysis; what is most important is the trend—how much does the grade change due to RTFO aging. It should be understood that a higher Δ signifies more premature age-hardening. The Δ Failure Temperature "Ultra High Performance Range" of less than 1.0° C. is denoted with the box on the graph. Remaining within this box signifies high resistance to premature age-hardening due to volatilization (caused by storing, heating, mixing, compacting, and other age-related factors) that occur at the very beginning of the asphalt's life cycle. Notably, all embodiments of the age-resistant AC composition invention fall within the Ultra High Performance Range, while the conventional PG 67-22 "premium" asphalt sample shows a trend towards excessive premature aging failure vulnerability. The chemical and physical properties of a representative conventional PG 67-22 compared to formulations 3A-3D are given in Table 11.

TABLE 11

Chemical and Physical Properties of a representative PG 67-22 asphalt compared to formulations 3A-3D.

| PARAMETER | TEST METHOD | RESULTS | | | | |
| | | PG 67-22 | 3A | 3B | 3C | 3D |
|---|---|---|---|---|---|---|
| Naphthene Aromatics | ASTM D | 44.0 | 46.4 | 49.0 | 51.5 | 51.0 |
| Polar Aromatics (Resins) | 4124 or IP | 30.4 | 32.2 | 34.4 | 34.5 | 35.7 |
| Saturates | 143 | 10.6 | 8.0 | 5.1 | 3.8 | 3.1 |

TABLE 11-continued

Chemical and Physical Properties of a representative PG 67-22 asphalt compared to formulations 3A-3D.

| PARAMETER | TEST METHOD | RESULTS | | | | |
|---|---|---|---|---|---|---|
| | | PG 67-22 | 3A | 3B | 3C | 3D |
| Asphaltenes | followed by IP 469 | 15.0 | 13.4 | 11.5 | 10.2 | 10.2 |
| Colloidal Index (CI) = ((NA + PA)/(S + A)) | N/A | | 2.9 | 4.3 | 5.9 | 6.8 | 7.0 |
| Physical Properties (Original Asphalt) | | | | | | |
| Penetration, dmm | AASHTO T 49 | 52 | 52 | 52 | 59 | 63 |
| Softening Point, ° C. | AASHTO T 53 | 53 | 51 | 52 | 51 | 51 |
| Physical Properties (Aging-Specific) AASHTO T 240-13 and AASHTO R 28 | | | | | | |
| Δ Failure Temp, ° C., G*/SIN (RTFO-Original) | AASHTO T 315 | 3.5 | 0.5 | −0.1 | 0 | 0 |
| Δ BBR Failure Temp, ° C. (RTFO + 40-hr PAV) − (RTFO + 20-hr PAV) | AASHTO T 313 | 3.9 | 2.2 | 2.2 | 2.3 | 2.0 |
| Δ BBR Failure Temp, ° C. (RTFO + 60-hr PAV) − (RTFO + 20-hr PAV) | | 7.8 | 4.1 | 4 | 5.4 | 5.1 |
| Δ Tc, ° C. (RTFO + 40-hr PAV) | | −3.1 | −0.4 | −0.6 | −1.7 | −1.0 |
| Δ Tc, ° C. (RTFO + 60-hr PAV) | | −6.8 | −1.9 | −2.5 | −3.0 | −2.8 |

Example 4—Aging Resistant Asphalt Compositions—Long-Term Aging Effects

Figure 3:
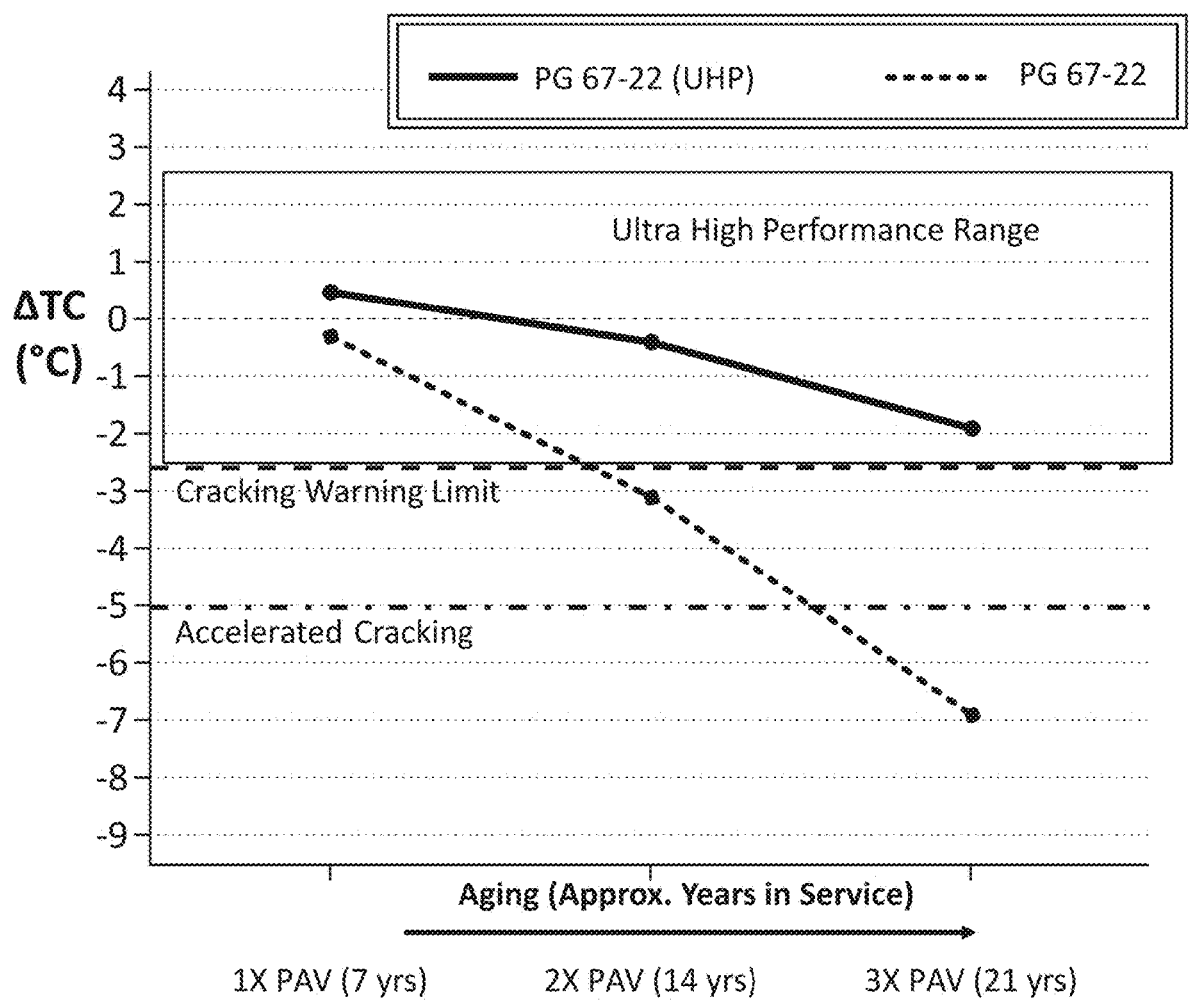
FIG. 3 is a graph of $\Delta T_c$ on the Y-axis against sample simulated age on the X-axis, comparing asphalt resistance to long-term aging for a PG 67-22 asphalt sample (dotted line) with an exemplary embodiment of an age-resistant asphalt composition of the invention that meets the criteria of PG 67-22 (solid line; "PG 67-22 (UHP)").

Now referring to FIG. 3, below, there is shown a comparison of the susceptibility to long-term aging-related distress between a conventional, premium PG-graded asphalt (labeled as "PG 67-22") and one embodiment (Example 3C) of the aging resistant asphalt composition (labeled as "PG 67-22 (UHP)"). Time points for Pressure Aging Vessel ("PAV")-simulated aging of 7 years, 14 years, and 21 years are plotted (PAV cycle multiples) on the X-axis. $\Delta T_c$ (° C.) is plotted on the Y-axis. The "Cracking Warning Limit" of $\Delta T_c$ (° C.) of minus (−) 2.5° C. and the "Accelerated Cracking" point of $\Delta T_c$ (° C.) of minus (−) 5.0° C. are shown on the graph. The $\Delta T_c$ "Ultra High Performance Range" of +/−2.5° C. is denoted with the box on the graph.

The 7-year simulation requires standard RTFO aging simulation according to AASHTO T240-13 followed by a 20-hour simulation (single cycle) of PAV aging according to AASHTO R 28-12 (2016). At the completion of the 20-hour simulation, the PAV rack, which contains all asphalt samples (some which have reached the desired number of PAV cycles and some which have not) is removed from the PAV. Pans of material which have reached the desired aging level are removed from the rack and further handled according to AASHTO T240-13 prior to further testing of those samples. Pans of material which have not yet reached the desired aging level remain on the rack and are re-loaded into the PAV for an additional 20-hour cycle for a total of 40 hours (2 cycles). The process is then repeated again for samples that have completed the desired number of aging cycles and for samples requiring an additional cycle for a total of 60 hours (3 cycles) of PAV aging. $\Delta T_c$ (° C.) is plotted on the Y-axis. $\Delta T_c$ trends downward (negative trend) over extended periods of time (beyond 7 years) for most asphalts. A lower (more negative) $\Delta T_c$ signifies higher susceptibility to age-hardening and cracking distress (additional explanation of this test parameter and its validity is given in the detailed description). Remaining within the "Ultra High Performance Range" box indicates high resistance to age-hardening and surface-induced cracking after the asphalt has been placed into service. As shown, $\Delta T_c$ places both asphalts in the Ultra High Performance Range (i.e., a $\Delta T_c$ within 2.5° C., which is the difference between m value and S(t) for the same asphalt regardless of aging level) at the 7-year mark (the maximum simulated aging requirement for current specifications). What is revealed after comparing the two asphalts for resistance to extended aging (beyond 7 years) and surface-initiated distress is extraordinary. The embodiment of the invention remained within the Ultra High Performance Range throughout the 21-year PAV aging simulation ($\Delta T_c$ net change of only about −2.0), while the conventional PG 67-22 "premium" asphalt sample shows a trend towards excessive long-term aging failure vulnerability ($\Delta T_c$ net change of about −6.5). The supposed "premium" conventional PG 67-22 asphalt declines rapidly towards the cracking limit and then into the accelerated cracking zone as defined by Anderson et al. (2011) well before reaching the typical 20+-year structural pavement design life. The cracking warning limit is surpassed at only 10-12 years, and the accelerated cracking limit is surpassed at approximately 17 years. Comparatively, the aging resistant asphalt composition PG 67-22 (UHP) remains above the cracking warning limit for the entire simulated 21-year cycle. By extrapolation, the aging resistant asphalt composition PG 67-22 (UHP) would not pass the cracking warning and the accelerated cracking limits until the 25-year and 40-year marks, respectively. This potentially translates to more than double the lifespan of resistance to aging and surface-initiated distress.

Of course, consideration must also be given to whether critical cold temperature would govern rather than $\Delta T_c$ after 25+ years in service. Comparison of extended aging resistance to critical cold temperature between a conventional, premium PG-graded asphalt (labeled as "PG 67-22") and an example embodiment (Example 3C) of the aging resistant asphalt composition (labeled as "PG 67-22 (UHP)"), is shown below in FIG. 4. The Y-axis is the BBR Failure Temperature (° C.) and the X-axis is time in multiples of seven (7)-year PAV-aging simulation cycles. The BBR failing temperature (Bending Beam Rheometer ("BBR") Failure Temperature) predicts the critical low temperature in which a particular asphalt can no longer resist thermal movements (expansion and contraction) due to increased stiffness and loss of relaxation properties. This graph relates to the low-temperature in the "PG 67-22" designation. The "-22" means that a particular asphalt can perform adequately in a cold temperature of approximately minus (−) 22° C. after approximately 7 years of aging (1×PAV cycle). Colder regions of the world may specify a lower temperature, such as −28° C. The opposite is true for warmer regions, such as −16° C. The grading occurs in 6° C. increments, so critical values falling between (−) 22° C. and (−) 27.9° C. are reported as −22° C. low temperature grade. Note that both asphalts in FIG. 4 meet the criteria for −22° C. grade at 7 years. Since both cold temperature and age-hardening account for the majority of stiffness increase and loss of relaxation properties in asphalt, the difference between each asphalt line (in which temperature is controlled) is attributed to the effects of age-hardening. The upper limit of the Ultra High Performance range will depend on the starting grade (and may therefore differ from this example), but the constant metric across all grades in which the invention applies is restricting the change in low-temperature grade to 5.0° C. between PAV-aging simulated 7 years and 21 years.

Figure 4:
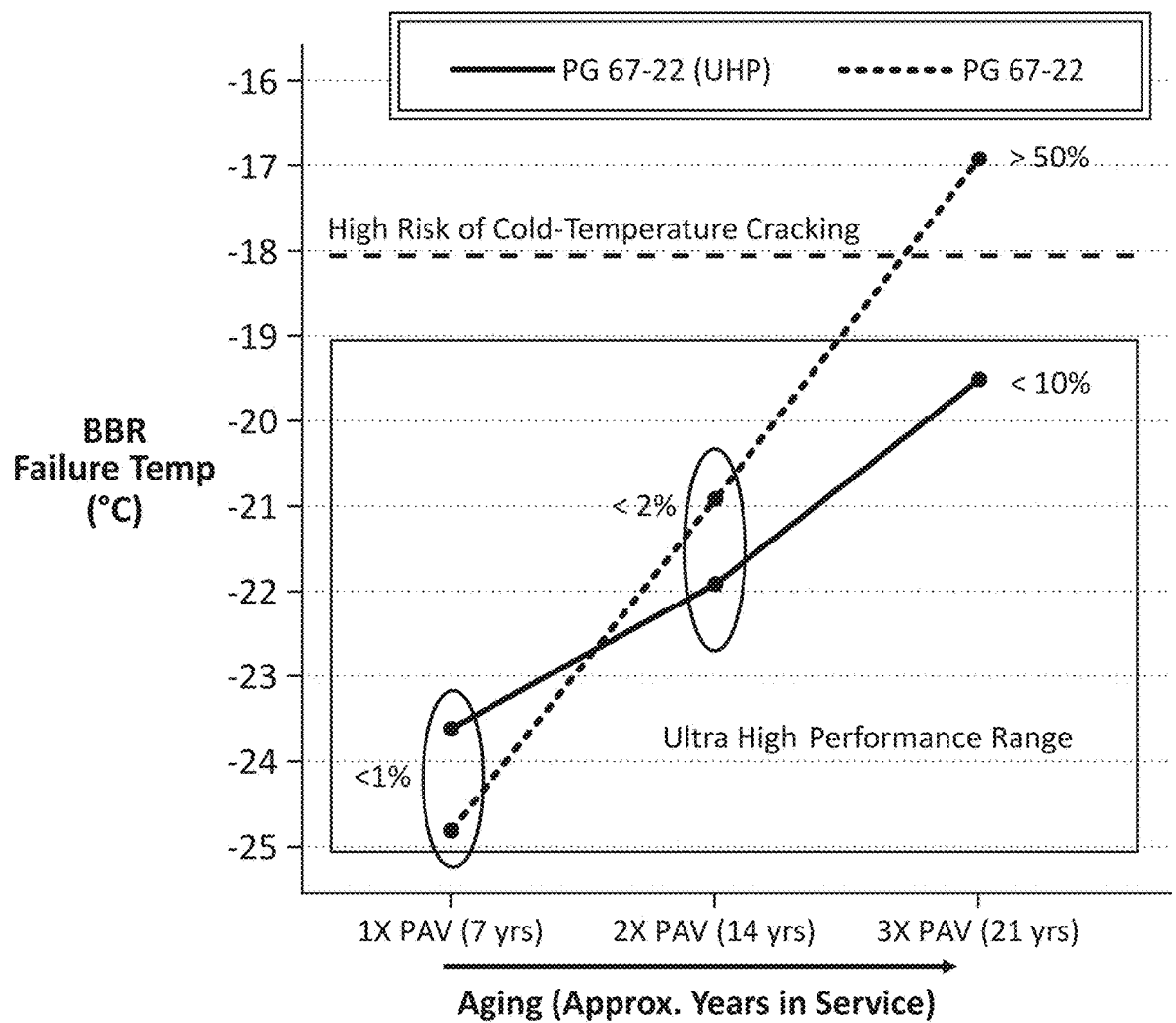
FIG. 4 is a graph of the BBR Failure Temperature on the Y-axis against sample simulated age on the X-axis, comparing asphalt resistance to extended aging-related distress for a conventional PG 67-22 asphalt sample (dotted line) against an exemplary embodiment of the invention meeting the criteria of PG 67-22 asphalt and age-resistant asphalt composition (solid line).

In FIG. 4, asphalt resistance to extended aging-related distress is expressed in terms of the decline in cold temperature failing grade (the increase in BBR Failure Temperature) for a conventional PG 67-22 asphalt sample (dotted line) and an exemplary embodiment of the invention meeting the criteria of PG 67-22 asphalt and age-resistant asphalt composition (solid line). The Y-axis is the BBR Failure Temperature (° C.) and the X-axis is time in multiples of seven (7)-year PAV-aging simulation cycles. The BBR Failure Temperature "Ultra High Performance Range" ensures that the asphalt maintains approximately less than a 5.0° C. loss in BBR failure temperature between PAV-aging simulated 7 years and 21 years. High Risk of Cold-Temperature Cracking (dashed line at −18° C.) appears at approximately 1.0° C. above the Ultra High Performance Range. The "%" shown at each time point is the estimated probability that a 1-day annual minimum pavement temperature will fall below the minimum failing temperature for the region.

As with premature aging resistance and $\Delta T_c$ extended aging resistance, the aging resistant asphalt composition PG 67-22 (UHP) also offers major improvement in resisting decline in cold-temperature PG grade due to aging. Based on the simulation of probability that a regional cold temperature event causes excessive surface-initiated cracking, it is evident that a conventional "premium" PG 67-22 asphalt is at great risk of this occurrence after approximately 17 years in service. Conversely, the aging resistant asphalt composition PG 67-22 UHP remains at relatively low risk of a failing cold temperature event throughout the entire simulated analysis period of 21 years. The example embodiment of the age-resistant AC composition invention remained within the Ultra High Performance Range throughout the simulated 21-year PAV aging simulation by losing only 4° C. in BBR failure temperature between PAV-aging simulated 7 years and 21 years, while the conventional PG 67-22 "premium" asphalt sample shows a trend towards excessive aging failure vulnerability as evidence by a loss of 8° C. in BBR failure temperature between PAV-aging simulated 7 years and 21 years. It should be understood that the PG 67-22 UHP exemplary embodiment meets the requirements of premium PG 67-22 performance grade paving asphalt in addition to the added aging resistance benefits shown in FIGS. 3 & 4.

Extending the serviceability and lifespan of well-designed and well-constructed AC pavements lies solely in overcoming the limitations related to asphalt durability and aging resistance. Any major improvement to the durability, age-resistance, and longevity of asphalt has the potential to transform societies that are so heavily reliant on an underfunded, rapidly deteriorating asphalt infrastructure to transport people, goods, and materials. For this to happen, even today's "good" asphalts must be considered as inherently flawed materials, and their performance must be considered over an extended aging period with respect to asphalt chemistry, microstructural behavior, macro-scale behavior, state-of-the-practice specifications, and state-of-the-art approaches designed to reveal flaws and weakness in asphalt performance. This broad approach is precisely what has led to the aging resistant asphalt compositions and methods provided herein.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A modified asphalt composition comprising a base asphalt and an aging resistance additive, wherein the modified asphalt composition has a colloidal index within the range of about 3.7 to about 8.0, a saturates content of less than about 10% by weight, and a measured change in BBR failure temperature of an RTFO plus 20-hour PAV-aged residue sample of the modified asphalt composition and an RTFO plus 60-hour PAV-aged residue sample of the modified asphalt composition is less than about 5.5° C., the asphalt composition further having a SARA fraction composition of about 40% to about 60% by weight naphthene aromatics, about 25% to about 45% by weight polar aromatics, and about 3% to about 15% by weight asphaltenes.

2. The modified asphalt composition of claim 1, wherein the base asphalt is a non-paving grade asphalt having a penetration value of about 0 dmm to about 40 dmm at 25° C. and a softening point greater than about 60° C.

3. The modified asphalt composition of claim 1, wherein the base asphalt is a paving grade asphalt.

4. The modified asphalt composition of claim 3, wherein the paving grade asphalt has a colloidal index of between about 3.1 and about 10.0.

5. The modified asphalt composition of claim 1, wherein the base asphalt has a SARA fraction composition of about 39% to about 63% by weight naphthene aromatics and about 22% to about 46% by weight polar aromatics.

6. The modified asphalt composition of claim 1, wherein the aging resistance additive comprises an oil blend with a SARA fraction composition of about 55% to about 80% by weight naphthene aromatics and about 10% to about 30% by weight polar aromatics.

7. The modified asphalt composition of claim 1, wherein the aging resistance additive has a colloidal index of greater than about 7.0 and less than about 100.

8. The modified asphalt composition of claim 1, wherein the aging resistance additive has a COC flash point between about 200° C. and about 300° C.

9. The modified asphalt composition of claim 1, wherein the aging resistance additive has a mass loss by % weight after RTFO aging according to AASHTO T 240 of between about 1.0 and about 3.0.

10. The modified asphalt composition of claim 1 further having a penetration value of between about 40 dmm and about 220 dmm at 25° C.

11. The modified asphalt composition of claim 1 wherein the SARA fraction composition of saturates in the asphalt composition is about 3% to about 8% by weight.

12. The modified asphalt composition of claim 1 further having a paraffin wax level of less than about 0.5%.

13. The modified asphalt composition of claim 1, wherein a measured difference between a high-temperature PG grade failure temperature from an original sample of the modified asphalt composition and a high-temperature PG grade failure temperature from an RTFO-aged residue sample of the modified asphalt composition is less than about 1.5° C.

14. The modified asphalt composition of claim 1, wherein a measured ΔTc of an RTFO plus 60-hour PAV-aged residue sample of the modified asphalt composition is between about 2.5° C. and about −5.0° C.

15. The modified asphalt composition of claim 14, wherein a measured ΔTc of an RTFO plus 60-hour PAV-aged residue sample of the modified asphalt composition is between about 2.5° C. and about −1.0° C.

16. The modified asphalt composition of claim 14, wherein a measured change in BBR failure temperature of an RTFO plus 20-hour PAV-aged residue sample of the modified asphalt composition and an RTFO plus 60-hour PAV-aged residue sample of the modified asphalt composition is less than about 3.0° C.

17. The modified asphalt composition of claim 1, wherein a measured G-R parameter value at 150 C and 0.005 rad/s of an RTFO plus 60-hour PAV-aged residue sample of the modified asphalt composition is less than 500.0 kPa.

18. The modified asphalt composition of claim 1, the modified asphalt composition having a measured G-R parameter value at 150 C and 0.005 rad/s of an RTFO plus 40-hour PAV-aged residue sample of the modified asphalt composition is less than 350.0 kPa.

19. The modified asphalt composition of claim 1, wherein the calculated crossover temperature calculated from the parameters of master curve developed with G-R frequency sweep test data at 15° C. reference temperature of an RTFO plus 60-hour PAV-aged residue sample of the modified asphalt composition is less than 32° C.

20. The modified asphalt composition of claim 1, wherein the crossover temperature calculated from the parameters of a master curve developed with G-R frequency sweep test data at 15° C. reference temperature of an RTFO plus 40-hour PAV-aged residue sample of the modified asphalt composition is less than 30° C.

21. The modified asphalt composition of claim 1, wherein a measured change in the naphthene aromatics fraction of a non-aged (original) sample of the modified asphalt composition and an RTFO plus 60-hour PAV-aged residue sample of the modified asphalt composition is less than about 45 percent.

22. The modified asphalt composition of claim 1, wherein a measured change in the polar aromatics (resins) fraction of a non-aged (original) sample of the modified asphalt composition and an RTFO plus 60-hour PAV-aged residue sample of the modified asphalt composition is less than about 100 percent.

23. The modified asphalt composition of claim 1, wherein a measured change in the asphaltenes fraction of a non-aged (original) sample of the modified asphalt composition and an RTFO plus 60-hour PAV-aged residue sample of the modified asphalt composition is less than about 25 percent.

24. The modified asphalt composition of claim 1, wherein a measured change in the colloidal index of a non-aged (original) sample of the modified asphalt composition and an RTFO plus 60-hour PAV-aged residue sample of the modified asphalt composition is less than about 25 percent.

25. The modified asphalt composition of claim 1, wherein a measured ΔTc of an RTFO plus 40-hour PAV-aged residue sample of the modified asphalt composition is between about 2.5° C. and about −3.0° C.

26. The modified asphalt composition of claim 1, wherein a measured change in BBR failure temperature of an RTFO plus 20-hour PAV-aged residue sample of the modified asphalt composition and an RTFO plus 40-hour PAV-aged residue sample of the modified asphalt composition is less than about 2.5° C.

* * * * *